United States Patent
Seitz et al.

(10) Patent No.: US 6,828,276 B2
(45) Date of Patent: Dec. 7, 2004

(54) HERBICIDALLY ACTIVE BENZOYLCYCLOHEXANEDIONES

(75) Inventors: Thomas Seitz, Viernheim (DE); Andreas van Almsick, Karben (DE); Lothar Willms, Hofheim (DE); Hermann Bieringer, Eppstein (DE); Thomas Auler, Bad Soden (DE); Hubert Menne, Hofheim (DE)

(73) Assignee: Aventis CropScience GmbH, Frankfurt (DE)

( * ) Notice: Subject to any disclaimer, the term of this patent is extended or adjusted under 35 U.S.C. 154(b) by 53 days.

(21) Appl. No.: 09/943,037

(22) Filed: Aug. 30, 2001

(65) Prior Publication Data

US 2002/0165095 A1 Nov. 7, 2002

(30) Foreign Application Priority Data

Sep. 1, 2000 (DE) .......................... 100 43 074

(51) Int. Cl.[7] .................... A01N 35/06; C07C 49/603
(52) U.S. Cl. .................... 504/221; 504/223; 504/236; 504/237; 504/238; 504/254; 504/269; 504/271; 504/287; 504/288; 504/289; 504/292; 504/299; 504/310; 504/326; 504/348; 544/3; 544/63; 544/238; 544/239; 544/240; 544/241; 546/288; 546/296; 546/297; 546/298; 548/213; 548/243; 548/366.7; 548/367.1; 548/369.4; 548/539; 549/28; 549/64; 549/294; 549/318; 549/322; 549/417; 549/477
(58) Field of Search ................... 544/3, 63, 238, 544/240, 241, 182, 96, 239; 568/28, 29, 31, 36, 37, 43, 329, 330; 504/130, 139, 238, 244, 254, 271, 282, 292, 294, 333, 348; 546/276.1, 298, 272.4; 548/110, 128, 131, 143, 203, 204, 214, 240, 247, 255, 266.2, 364.1, 365.7, 312.4; 549/427, 498; 564/99

(56) References Cited

U.S. PATENT DOCUMENTS

| | | | |
|---|---|---|---|
| 4,440,940 A | 4/1984 | Shepherd et al. | 560/19 |
| 4,969,825 A | 11/1990 | Oya et al. | 71/92 |
| 5,712,298 A | 1/1998 | Amschler | 514/352 |
| 5,935,978 A | 8/1999 | Fenton et al. | 514/352 |

FOREIGN PATENT DOCUMENTS

| | | |
|---|---|---|
| EP | 0 579 223 | 1/1994 |
| GB | 2 061 913 | 5/1981 |
| WO | WO 98/41089 | 9/1998 |
| WO | WO 99/10327 | 3/1999 |

OTHER PUBLICATIONS

Patent Abstracts of Jpan, 10059929, published Mar. 3, 1998, vol. 1998, No. 8.
Patent Abstracts of Japan, 06271562, published Sep. 27, 1994, vol. 18, No. 680.

*Primary Examiner*—Richard L. Raymond
(74) *Attorney, Agent, or Firm*—Frommer Lawrence & Haug LLP

(57) ABSTRACT

There are described benzoylcyclohexanediones of the formula I, their preparation, and their use as herbicides and plant growth regulators.

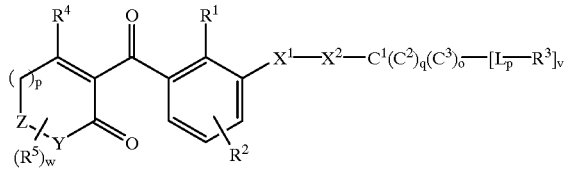

In this formula (I), $C^1$, $C^2$, $C^3$ are cyclic radicals, $X^1$ is a hetero atom, $X^2$ is a chain of carbon atoms, L is a chain-like element, $R^1$, $R^2$, $R^3$, $R^4$, $R^5$ are various radicals, and Y and Z are monoatomic bridge elements.

18 Claims, No Drawings

HERBICIDALLY ACTIVE BENZOYLCYCLOHEXANEDIONES

The invention relates to the technical field of the herbicides, in particular that of the herbicides for selectively controlling broad-leaved weeds and grass weeds in crops of useful plants.

It has already been disclosed in various publications that certain benzoylcyclohexanediones, including those which are substituted in the 3-position of the phenyl ring, for example by a cyclic radical, have herbicidal properties. WO 99/10327 discloses benzoylcyclohexanediones which have attached to them in the 3-position of the phenyl ring a heterocyclic radical containing at least one nitrogen atom and bonded via a chain of carbon atoms. WO 00/21924 mentions benzoylcyclohexanediones which have attached to them in the 3-position of the phenyl ring a heterocyclic or carbocyclic radical which is bonded via a chain of carbon atoms.

However, the application of the compounds disclosed in these publications frequently entails disadvantages in practice. Thus, the herbicidal activity of the known compound is not always sufficient, or, when the herbicidal activity is sufficient, undesired crop plant damage is observed. It was therefore an object of the present invention to provide herbicidally active compounds which have improved herbicidal properties over the compounds known from the prior art.

It has now been found that benzoylcyclohexanediones which have attached to them in the 3-position of the phenyl ring certain cyclic radicals which are bonded via an oxygen, nitrogen or sulfur atom are particularly suitable as herbicides. Subject matter of the present invention are therefore compounds of the formula (I) or their salts

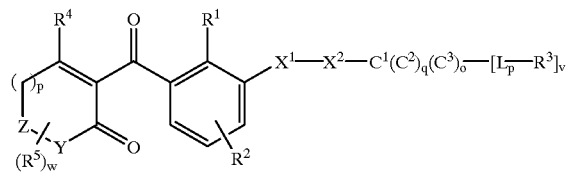

(I)

in which $X^1$ is a divalent unit selected from the group consisting of O, $S(O)_n$, NH, $N[L_p-R^3]$;

$X^2$ is a straight-chain or branched $(C_1-C_6)$-alkylene, $(C_2-C_6)$-alkenylene or $(C_2-C_6)$-alkynylene chain which is substituted by w halogen atoms;

$C^1(C^2)_q(C^3)_o$ is a mono-, bi- or tricyclic radical, where
a) the rings $C^1$, $C^2$ and $C^3$ are in each case a 3- to 8-membered, saturated or partially saturated ring selected from the group consisting of cycloalkyl, cycloalkenyl, oxiranyl and oxetanyl,
b) the rings $C^1$, $C^2$ and $C^3$ are in each case linked to each other via one or two joint atoms;

$R^1$ and $R^2$ independently of one another are hydrogen, mercapto, nitro, cyano, halogen, thiocyanato, $(C_1-C_6)$-alkyl-CO—O, $(C_1-C_6)$-alkyl-$S(O)_n$—O, $(C_1-C_6)$-alkyl-S$(O)_n$, di-$(C_1-C_6)$-alkyl-NH—$SO_2$, $(C_1-C_6)$-alkyl-$SO_2$—NH, $(C_1-C_6)$-alkyl-NH—CO, $(C_1-C_6)$-alkyl—$SO_2$—$[(C_1-C_6)$-alkyl]amino, $(C_1-C_6)$-alkyl-CO—$((C_1-C_6)$-alkyl)amino, 1,2,4-triazol-1-yl, $(C_1-C_6)$-alkyl-O—$CH_2$, $(C_1-C_6)$-alkyl-$S(O)_n$—$CH_2$, $(C_1-C_6)$-alkyl-NH—$CH_2$, $[(C_1-C_6)$-alkyl]$_2$N—$CH_2$, 1,2,4-triazol-1-yl-$CH_2$, or are $(C_1-C_6)$-alkyl-$(D)_p$, $(C_2-C_6)$-alkenyl-$(D)_p$, $(C_2-C_6)$-alkynyl-$(D)_p$, $(C_3-C_9)$-cycloalkyl-$(D)_p$, $(C_3-C_9)$-cycloalkenyl-$(D)_p$, $(C_1-C_6)$-alkyl-$(C_3-C_9)$-cycloalkyl-$(D)_p$ or $(C_1-C_6)$-alkyl-$(C_3-C_9)$-cycloalkenyl-$(D)_p$, each of which is substituted by v radicals selected from the group consisting of cyano, nitro and halogen;

$R^3$ is hydrogen, hydroxyl, halogen, mercapto, amino, nitro, a carbon-containing radical or, if p in $X^1$ is zero, $R^3$ is oxo, $NR^8$, N—$OR^8$ or N—$NR^8R^9$;

D is oxygen or sulfur;

L is in each case straight-chain or branched $A_p$-$[C(R^6)_2]_w$-$[A_p$-$C(R^6)_2]_x$-$A_p$ or $A_p$-M-$A_p$;

with the proviso that 2 or 3 of the variable terms p, w and x shall not simultaneously be zero;

A is a divalent unit selected from the group consisting of O, $S(O)_n$, NH, N—$(C_1-C_6)$-alkyl, N—$(C_2-C_6)$-alkenyl and N—$(C_2-C_6)$-alkynyl;

M is $(C_1-C_6)$-alkylene, $(C_2-C_6)$-alkenylene or $(C_2-C_6)$-alkynylene, each of which is substituted by w radicals $R^6$;

$R^4$ is $OR^7$, $(C_1-C_4)$-alkylthio, halo-$(C_1-C_4)$-alkylthio, $(C_1-C_4)$-alkenylthio, halo-$(C_2-C_4)$-alkenylthio, $(C_2-C_4)$-alkynylthio, halo-$(C_2-C_4)$-alkynylthio, $(C_2-C_4)$-alkylsulfinyl, halo-$(C_2-C_4)$-alkylsulfinyl, $(C_2-C_4)$-alkenylsulfinyl, halo-$(C_2-C_4)$-alkenylsulfinyl, $(C_2-C_4)$-alkynylsulfinyl, halo-$(C_2-C_4)$-alkynylsulfinyl, $(C_1-C_4)$-alkylsulfonyl, halo-$(C_1-C_4)$-alkylsulfonyl, $(C_2-C_4)$-alkenylsulfonyl, halo-$(C_2-C_4)$-alkenylsulfonyl, $(C_2-C_4)$-alkynylsulfonyl, halo-$(C_2-C_4)$-alkynylsulfonyl, cyano, cyanato, thiocyanato, halogen or phenylthio;

$R^5$ is hydrogen, tetrahydropyran-3-yl, tetrahydropyran-4-yl, tetrahydrothiopyran-3-yl, $(C_1-C_4)$-alkyl, $(C_3-C_8)$-cycloalkyl, $(C_1-C_4)$-alkoxy, $(C_1-C_4)$-alkoxy-$(C_1-C_4)$-alkyl, $(C_1-C_4)$-alkylcarbonyl, $(C_1-C_4)$-alkoxycarbonyl, $(C_1-C_4)$-alkylthio, phenyl, the eight last-mentioned groups being substituted by v radicals selected from the group consisting of halogen, $(C_1-C_4)$-alkylthio and $(C_1-C_4)$-alkoxy, or two radicals $R^5$ bonded to a joint carbon atom form a chain selected from the group consisting of $OCH_2CH_2O$, $OCH_2CH_2CH_2O$, $SCH_2CH_2S$ and $SCH_2CH_2CH_2S$, this group being substituted by w methyl groups, or two radicals $R^5$ bonded to directly adjacent carbon atoms, together with the carbon atoms to which they are attached, form a 3- to 6-membered ring which is substituted by w radicals selected from the group consisting of halogen, $(C_1-C_4)$-alkyl, $(C_1-C_4)$-alkylthio and $(C_1-C_4)$-alkoxy;

$R^6$ is $(C_1-C_4)$-alkyl, halogen, cyano or nitro;

$R^7$ is hydrogen, $(C_1-C_4)$-alkyl, halo-$(C_1-C_4)$-alkyl, $(C_1-C_4)$-alkoxy-$(C_1-C_4)$-alkyl, formyl, $(C_1-C_4)$-alkylcarbonyl, $(C_1-C_4)$-alkoxycarbonyl, $(C_1-C_4)$-alkylaminocarbonyl di-$(C_1-C_4)$-alkylaminocarbonyl, $(C_1-C_4)$-alkylsulfonyl, halo-$(C_1-C_4)$-alkylsulfonyl, benzoyl or phenylsulfonyl, the two last-mentioned groups being substituted by v radicals selected from the group consisting of $(C_1-C_4)$-alkyl, halo-$(C_1-l_4)$-alkyl, $(C_1-C_4)$-alkoxy, halo-$(C_1-C_4)$-alkoxy, halogen, cyano and nitro;

$R^8$ is hydrogen, $(C_1-C_4)$-alkyl, $(C_1-C_4)$-alkoxy, $(C_2-C_4)$-alkenyl, $(C_2-C_4)$-alkynyl, $(C_3-C_8)$-cycloalkyl, aryl, aryl-$(C_1-C_6)$-alkyl, heteroaryl, heterocyclyl, halo-$(C_1-C_4)$-alkyl;

$R^9$ is hydrogen, $(C_1-C_4)$-alkyl, $(C_2-C_4)$-alkenyl, $(C_2-C_4)$-alkynyl, $(C_3-C_9)$-cycloalkyl, aryl, aryl-$(C_1-C_6)$-alkyl, heteroaryl, heterocyclyl, halo-$(C_1-C_4)$-alkyl, or, if $R^8$ and $R^9$ are bonded to one atom or to two directly adjacent atoms, they together with the atoms to which they are bonded form a saturated, partially or fully unsaturated five- to six-membered ring which contains p hetero atoms selected from the group consisting of oxygen, nitrogen and sulfur;

Y is a divalent unit selected from the group consisting of O, S, N—H, N—$(C_1$–$C_4)$-alkyl, $CHR^5$ and $C(R^5)_2$;

Z is a divalent unit selected from the group consisting of O, S, SO, $SO_2$, N—H, N—$(C_1$–$C_4)$-alkyl, $CHR^5$ and $C(R^5)_2$;

m and n are each 0, 1 or 2;

o, p and q are each 0 or 1;

w and x are each 0, 1, 2, 3 or 4;

v is 0, 1, 2 or 3.

Depending on external conditions such as solvent and pH, a large number of compounds of the formula (I) according to the invention can occur in different tautomeric structures. Depending on the nature of the substituents, the compounds of the formula (I) contain an acidic proton, which can be removed by reaction with a base. Examples of suitable bases are hydrides, hydroxides and carbonates of lithium, sodium, potassium, magnesium and calcium, and ammonia and organic amines such as triethylamine and pyridine. Such salts are also subject matter of the invention.

In all of the formulae mentioned hereinbelow, the substituents and symbols, unless otherwise defined, have the same meaning as described under formula (I).

In formula (I) and all subsequent formulae, chain-like carbon-containing radicals such as alkyl, alkoxy, haloalkyl, haloalkoxy, alkylamino and alkylthio and the corresponding radicals which are unsaturated and/or substituted in the carbon skeleton, such as alkenyl and alkynyl, can in each case be straight-chain or branched. Unless specifically indicated, the lower carbon skeletons, for example those having 1 to 6 carbon atoms or, in the case of unsaturated groups, those having 2 to 4 carbon atoms, are preferred among these radicals. Alkyl radicals, also in the composite meanings such as alkoxy, haloalkyl and the like, are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals have the meanings of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl. The multiple bond can be located at any desired position of the unsaturated radical.

Unless specifically indicated, cycloalkyl is a carbocyclic saturated ring system having three to eight carbon atoms, for example cyclopropyl, cyclopentyl or cyclohexyl. Analogously, cycloalkenyl is a monocyclic alkenyl group having three to eight carbon ring members, for example cyclobutenyl, cyclopentenyl and cyclohexenyl, it being possible for the double bond to be located at any desired position. If o and/or q equal(s) 1, the radical $C^1(C^2)_q(C^3)_o$ is present as bi- or tricyclic radical. Examples are adamantyl, bicyclo[4.1.0]heptanyl, bicyclo[3.2.0]heptanyl, bicyclo[4.2.0]octanyl, bicyclo[3.3.0]octanyl, bicyclo[4.3.0]nonanyl, bicyclo[4.3.0]non-1-enyl, bicyclo[2.2.1]hept-2-enyl, bicyclo[2.2.2]oct-2-enyl, bicyclo[3.1.1]hept-2-enyl, bicyclo[3.3.1]non-2-enyl, spiro[2.2]pentanyl and dispiro[2.2.1]heptanyl.

In the case of a bisubstituted amino group, such as dialkylamino, these two substituents can be identical or different.

Halogen is fluorine, chlorine, bromine or iodine. Haloalkyl, -alkenyl and -alkynyl are alkyl, alkenyl or alkynyl which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this also applies analogously to haloalkenyl and other halogen-substituted radicals.

The term heterocyclyl is to be understood as meaning the radicals of three- to nine-membered, saturated, partially or fully unsaturated heterocycles which contain one to three hetero atoms selected from the group consisting of oxygen, nitrogen and sulfur. If chemically possible, the linkage can be effected at any desired position of the heterocycle. Heterocyclyl is preferably aziridinyl, oxiranyl, tetrahydrofuranyl, tetrahydropyranyl, tetrahydrothienyl, pyrrolidinyl, isoxazolidinyl, isoxazolinyl, thiazolinyl, thiazolidinyl, pyrazolidinyl, morpholinyl, piperidinyl, dioxolanyl, dioxanyl, piperazinyl, oxepanyl, azepanyl.

Heteroaryl is the radical of a heteroaromatic ring which, in addition to carbon ring members, contains one to five hetero atoms selected from the group consisting of nitrogen, oxygen and sulfur. Heteroaryl is preferably furanyl, thienyl, pyrrolyl, pyrazolyl, imidazolyl, oxazolyl, thiazolyl, isoxazolyl, isothiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, pyridyl, pyridazinyl, pyrimidinyl, pyrazinyl, 1,2,4-triazinyl, 1,3,5-triazinyl.

Aryl is an aromatic mono- or polycyclic hydrocarbon radical, for example phenyl, naphthyl, biphenyl and phenanthryl.

If a group or a radical is polysubstituted, this is to be understood as meaning that the general principles of the construction of chemical compounds must be taken into consideration when combining the various substituents, i.e. that the formation of compounds which are known to the skilled worker as being chemically unstable or impossible must be avoided. This also applies analogously to the linkages of individual radicals.

If a group or a radical is polysubstituted by other radicals, these other radicals can be identical or different. If a heterocyclic radical is hydroxyl-substituted, this definition is also to be understood as encompassing the tautomeric form of the oxo group.

Depending on the nature and linkage of the substituents, the compounds of the formula (I) can exist as stereoisomers. If, for example, one or more alkenyl groups are present, diastereomers may occur. If, for example, one or more asymmetric carbon atoms are present, enantiomers and diastereomers may occur. Stereoisomers can be obtained by customary separation methods, for example by chromatographic separation methods, from the mixtures which the preparation yields. Likewise, stereoisomers can be prepared selectively by employing stereo-selective reactions using optically active starting materials and/or auxiliaries. The invention also relates to all stereoisomers and their mixtures which are encompassed by formula (I), but not specifically defined.

The condition that "Y" and "Z" are not simultaneously in each case one divalent unit with hetero atoms shall apply to the choice of the meanings for "Y" and "Z".

A carbon-containing radical is to be understood as meaning a radical with at least one carbon atom and several identical or different atoms selected from the group consisting of hydrogen, halogen, oxygen, nitrogen, sulfur and phosphorus. This definition is to be understood as meaning in particular the following radicals:

a) cyano, formyl;

b) aryl which is substituted by w radicals selected from the group consisting of halogen, cyano, nitro, formyl, $(C_1-C_4)$-alkyl, halo-$(C_1-C_4)$-alkyl, $(C_1-C_4)$-alkoxy, halo-$(C_1-C_4)$-alkoxy, $(C_1-C_4)$-alkylthio, halo-$(C_1-C_4)$-alkylthio and $R^{10}$, or else mono- or bicyclic heterocyclyl or heteroaryl, each of which contains one to four hetero atoms selected from the group consisting of oxygen, nitrogen and sulfur;

c) $(R^{11})(C_1-C_4)$-alkylamino, $(R^{11})_2$-amino, $R^{11}$-oxycarbonyl, $R^{11}$-carbonyl, $R^{11}$-carbonyloxy; $(C_1-C_6)$-alkyl, $(C_2-C_6)$-alkenyl, $(C_2-C_6)$-alkynyl, $(C_1-C_6)$-alkoxy-$(C_1-C_6)$-alkyl, $(C_2-C_6)$-alkenyloxy-$(C_1-C_6)$-alkyl, $(C_2-C_6)$-alkynyloxy-$(C_1-C_6)$-alkyl, $(C_3-C_9)$-cycloalkyl, $(C_3-C_9)$-cyloalkenyl, $(C_2-C_6)$-alkenyl-$(C_3-C_9)$-cycloalkyl, $(C_2-C_6)$-alkenyl-$(C_3-C_9)$-cycloalkyl-$(C_1-C_6)$-alkyl, $(C_2-C_6)$-alkenyl-$(C_3-C_9)$-cycloalkenyl, $(C_2-C_6)$-alkylenyl-$(C_3-C_9)$-cycloalkenyl-$(C_1-C_6)$-alkyl, $(C_2-C_6)$-alkenyl-$(C_3-C_9)$-cycloalkyl, $(C_2-C_6)$-alkenyl-$(C_3-C_9)$-cycloalkyl-$(C_1-C_6)$-alkyl, $(C_2-C_6)$-alkenyl-$(C_3-C_9)$-cycloalkenyl, $(C_2-C_6)$-alkenyl-$(C_3-C_9)$-cycloalkenyl-$(C_1-C_6)$-alkyl, $(C_2-C_6)$-alkynyl-$(C_3-C_9)$-cycloalkyl, $(C_2-C_6)$-alkynyl-$(C_3-C_9)$-cycloalkyl-$(C_1-C_6)$-alkyl, $(C_2-C_6)$-alkynyl-$(C_3-C_9)$-cycloalkenyl, $(C_2-C_6)$-alkynyl-$(C_3-C_9)$-cycloalkenyl-$(C_1-C_6)$-alkyl, $(C_1-C_6)$-alkoxy or $(C_1-C_6)$-alkylthio, each of which is substituted by w radicals selected from the group consisting of formyl, halogen, cyano, nitro, $(C_1-C_4)$-alkylamino, $(C_1-C_4)$-dialkylamino, $(C_1-C_4)$-alkoxycarbonyl, $(C_1-C_4)$-alkylcarbonyl, $(C_1-C_4)$-alkylcarbonyloxy, $(C_1-C_4)$-alkyl, $(C_2-C_4)$-alkenyl, $(C_2-C_4)$-alkynyl, halogen-$(C_1-C_4)$-alkyl, $(C_2-C_4)$-haloalkenyl, $(C_2-C_4)$-haloalkynyl, $(C_1-C_4)$-alkylthio, halo-$(C_1-C_4)$-alkylthio, $(C_1-C_4)$-alkoxy and halo-$(C_1-C_4)$-alkoxy;

d) a radical of the formula (Va) to (Vz-3):

In these formulae, the substituents have the following meanings:

$R^{10}$ is $[(C_1-C_4)\text{-alkylene-O-}(C_1-C_4)\text{-alkylene}]_o$-O-$(C_1-C_4)$-alkyl, or else $(C_1-C_4)$-alkyl, $(C_2-C_4)$-alkenyl or $(C_2-C_4)$-alkynyl, each of which is substituted by v radicals selected from the group consisting of halogen, cyano and nitro;

$R^{11}$ and $R^{12}$ independently of one another are hydrogen, or else $(C_1-C_6)$-alkyl, $(C_2-C_6)$-alkenyl, $(C_2-C_6)$-alkynyl, $(C_1-C_6)$-alkoxy-$(C_1-C_6)$-alkyl, $(C_2-C_6)$-alkenyloxy-$(C_1-C_6)$-alkyl, $(C_2-C_6)$-alkynyloxy-$(C_1-C_6)$-alkyl, $(C_3-C_9)$-cycloalkyl, $(C_3-C_9)$-cycloalkenyl, $(C_1-C_6)$-alkyl-$(C_3-C_9)$-cycloalkyl, $(C_1-C_6)$-alkyl-$(C_3-C_9)$-cycloalkyl-$(C_1-C_6)$-alkyl, $(C_1-C_6)$-alkyl-$(C_3-C_9)$-cycloalkenyl, $(C_1-C_6)$-alkyl-$(C_3-C_9)$-cycloalkenyl-$(C_1-C_6)$-alkyl, $(C_2-C_6)$-alkenyl-$(C_3-C_9)$-cycloalkyl, $(C_2-C_6)$-alkenyl-$(C_3-C_9)$-cycloalkyl-$(C_1-C_6)$-alkyl, $(C_2-C_6)$-alkenyl-$(C_3-C_9)$-cycloalkenyl, $(C_2-C_6)$-alkenyl-$(C_3-C_9)$-cycloalkenyl-$(C_1-C_6)$-alkynylcycloalkyl, $(C_2-C_6)$-alkynyl-$(C_3-C_9)$-cycloalkyl-$(C_1-C_6)$-alkyl, $(C_2-C_6)$-alkynylcycloalkyl $(C_2-C_6)$-alkynyl-$(C_3-C_9)$-cycloalkyl-$(C_1-C_6)$-alkyl, $(C_2-C_6)$-alkynyl-$(C_3-C_9)$-cycloalkenyl, $(C_2-C_6)$-alkynyl-$(C_3-C_9)$-cycloalkenyl-$(C_1-C_6)$-alkyl, aryl, aryl-$(C_1-C_6)$-alkyl, aryl-$(C_2-C_6)$-alkenyl, each of which is substituted by v radicals selected from the group consisting of halogen, cyano and nitro, or $R^{11}$ and $R^{12}$ together with the atoms to which they are bonded form a saturated, partially or fully unsaturated five- to six-membered ring which, in addition to carbon atoms, contains p hetero atoms selected from the group consisting of oxygen, nitrogen and sulfur;

Compounds of the formula I which are of greater interest are those in which $X^1$ is a divalent unit selected from the group consisting of O, S and NH;

$R^1$ is chlorine, bromine, fluorine, methyl, ethyl, cyano, nitro, halo-$(C_1-C_2)$-alkyl;

$R^2$ is halogen, halo-$(C_1-C_4)$-alkyl, $(C_1-C_4)$-alkylsulfenyl, $(C_1-C_4)$-alkylsulfinyl, $(C_1-C_4)$-alkylsulfonyl or nitro;

$R^5$ is $(C_1-C_4)$-alkyl, $(C_3-C_8)$-cycloalkyl, $(C_1-C_4)$-alkoxy, $(C_1-C_4)$-alkoxy-$(C_1-C_4)$-alkyl, $(C_1-C_4)$-alkylcarbonyl, $(C_1-C_4)$-alkoxycarbonyl, $(C_1-C_4)$-alkylthio, phenyl, or two radicals $R^5$ bonded to a joint carbon atom form a chain selected from the group consisting of $OCH_2CH_2O$, $OCH_2CH_2CH_2O$, $SCH_2CH_2S$ and $SCH_2CH_2CH_2S$, this group being substituted by w methyl groups, or two radicals $R^5$ bonded to directly adjacent carbon atoms form a bond or, together with the carbon atoms to which they are attached, form a 3- to 6-membered ring which is substituted by w radicals selected from the group consisting of halogen, $(C_1-C_4)$-alkyl, $(C_1-C_4)$-alkylthio and $(C_1-C_4)$-alkoxy;

$R^8$ is hydrogen, $(C_1-C_4)$-alkyl, $(C_1-C_4)$-alkoxy, $(C_2-C_4)$-alkenyl, $(C_2-C_4)$-alkynyl, $(C_3-C_8)$-cycloalkyl, aryl, aryl-$(C_1-C_6)$-alkyl, halo-$(C_1-C_4)$-alkyl;

$R^9$ is hydrogen, $(C_1-C_4)$-alkyl, or, if $R^8$ and $R^9$ are bonded to one atom or to two directly adjacent atoms, they together with the atoms to which they are bonded form a saturated, partially or fully unsaturated five- to six-membered ring which contains p hetero atoms selected from the group consisting of oxygen, nitrogen and sulfur.

Compounds of the formula I which are of particular interest are those in which $X^2$ is a straight-chain or branched $(C_1-C_4)$-alkylene, $(C_2-C_4)$-alkenylene or $(C_2-C_4)$-alkynylene chain, each of which is substituted by w halogen atoms;

$R^3$ is
a) hydrogen, hydroxyl, halogen, mercapto, amino, nitro, cyano, formyl, b) phenyl, oxazolyl, furanyl or tetrahydropyrrolyl, each of which is substituted by w radicals selected from the group consisting of halogen, cyano, $(C_1-C_4)$-alkyl, halo-$(C_1-C_4)$-alkyl, $(C_1-C_4)$-alkoxy, halo-$(C_1-C_4)$-alkoxy, $(C_1-C_4)$-alkylthio, halo-$(C_1-C_4)$-alkylthio and $R^{10}$, c) $(R^{11})(C_1-C_4)$-alkylamino, $(R^{11})_2$-amino, $R^{11}$-oxycarbonyl, $R^{11}$-carbonyl, $R^{11}$-carbonyloxy; $(C_1-C_6)$-alkyl, $(C_2-C_6)$-alkenyl, $(C_2-C_6)$-alkynyl, $(C_1-C_6)$-alkoxy-$(C_1-C_6)$-alkyl, $(C_2-C_6)$-alkynyloxy-$(C_1-C_6)$-alkyl, $(C_3-C_9)$-cycloalkyl, $(C_3-C_9)$-cyloalkenyl, $(C_1-C_6)$-alkoxy or $(C_1-C_6)$-alkylthio, each of which is substituted by v radicals selected from the group consisting of formyl, halogen, cyano, nitro, $(C_1-C_4)$-alkylamino, $(C_1-C_4)$-dialkylamino, $(C_1-C_4)$-alkoxycarbonyl, $(C_1-C_4)$-alkylcarbonyl, $(C_1-C_4)$-alkylcarbonyloxy, $(C_1-C_4)$-alkyl, $(C_2-C_4)$-alkenyl, $(C_2-C_4)$-alkynyl, halo-$(C_1-C_4)$-alkyl, $(C_1-C_4)$-alkylthio, halo-$(C_1-C_4)$-alkylthio, $(C_1-C_4)$-alkoxy and halo-$(C_1-C_4)$-alkoxy;

d) a radical of the formula Va, Vb, Vc, Vd, Vj or Vp, or e) if p is zero, oxo, $NR^8$, N—$OR^8$ or N—$NR^8R^9$;

$R^7$ is hydrogen, $(C_1-C_4)$-alkylsulfonyl, benzoyl or phenylsulfonyl, the two last-mentioned groups being substituted by v radicals selected from the group consisting of $(C_1-C_2)$-alkyl, halo-$(C_1-C_2)$-alkyl, $(C_1-C_2)$-alkoxy, halo-$(C_1-C_2)$-alkoxy, halogen, cyano and nitro, and $R^{11}$ is hydrogen, $(C_1-C_4)$-alkyl, $(C_2-C_4)$-alkenyl, $(C_2-C_4)$-alkynyl or $(C_3-C_8)$-cycloalkyl.

Preferred compounds of the formula I are those in which $X^1$ is the divalent unit O;

$R^4$ is $OR^7$, $(C_1-C_4)$-alkylthio, $(C_2-C_4)$-alkenylthio, $(C_1-C_4)$-alkylsulfonyl, cyano, cyanato, thiocyanato, or else phenylthio which is substituted by v radicals selected from the group consisting of halogen, $(C_1-C_2)$-alkyl, $(C_1-C_2)$-alkoxy, halo-$(C_1-C_2)$-alkyl, halo-$(C_1-C_2)$-alkoxy and nitro;

$R^5$ is hydrogen, $(C_1-C_4)$-alkyl, $(C_3-C_8)$-cycloalkyl, $(C_1-C_4)$-alkoxy, $(C_1-C_4)$-alkylthio, phenyl, or two radicals $R^5$ bonded to directly adjacent carbon atoms, together with the carbon atoms to which they are bonded, form a substituted 3- to 6-membered ring;

$R^{12}$ is hydrogen, $(C_1-C_4)$-alkyl, $(C_2-C_4)$-alkenyl, or, if $R^{11}$ and $R^{12}$ are bonded to one atom or to two directly adjacent atoms, they together with the atoms to which they are bonded form a saturated, partially or fully unsaturated five- to six-membered ring which contains p hetero atoms selected from the group consisting of oxygen, nitrogen and sulfur;

Y is a divalent unit selected from the group consisting of $CHR^5$ and $C(R^5)_2$, and Z is a divalent unit selected from the group consisting of O, S, $SO_2$, N—$(C_1-C_4)$-alkyl, $CHR^5$ and $C(R^5)_2$.

Likewise preferred compounds of the formula I are those in which $R^2$ is halogen, halo-$(C_1-C_2)$-alkyl or $(C_1-C_2)$-alkylsulfonyl;

$R^5$ is $(C_1-C_4)$-alkyl, $(C_3-C_8)$-cycloalkyl, $(C_1-C_4)$-alkoxy, $(C_1-C_4)$-alkylthio, phenyl, or two radicals $R^5$ bonded to directly adjacent carbon atoms together with the carbon atoms to which they are attached form a substituted 3- to 6-membered ring;

$R^7$ is hydrogen, $(C_1-C_4)$-alkylsulfonyl, benzoyl or phenylsulfonyl, and $R^8$ is hydrogen, methyl or ethyl, and $R^2$ is in the 4-position of the phenyl ring.

Especially preferred compounds of the formula I are those in which $X^2$ is a straight-chain or branched $(C_1-C_4)$-alkylene, $(C_2-C_4)$-alkenylene or $(C_2-C_4)$-alkynylene chain;

$R^1$ is chlorine, bromine, methyl, trifluoromethyl, cyano or nitro;

$R^2$ is chlorine, bromine, methylsulfonyl, ethylsulfonyl, trifluoromethyl or nitro;

$R^4$ is $OR^7$, $(C_1-C_4)$-alkylthio, $(C_2-C_4)$-alkenylthio or phenylthio;

$R^5$ is hydrogen, $(C_1-C_4)$-alkyl, or two radicals $R^5$ bonded to directly adjacent carbon atoms together with the carbon atoms to which they are attached form a substituted 3- to 6-membered ring;

A is a divalent unit selected from the group consisting of O, $S(O)_n$, NH and N—$(C_1-C_6)$-alkyl;

M is $(C_1-C_6)$-alkylene;

Y and Z independently of one another are a divalent unit selected from the group consisting of $CHR^5$ and $C(R^5)_2$.

Depending on the meanings of the substituents, the compounds according to the invention can be prepared for example by one or more of the processes stated in the schemes which follow.

Compounds of the formula (I) according to the invention can be prepared in accordance with processes known per se by reacting a cyclohexanedione of the formula (II) with the benzoyl derivative of the formula (III) in which T is halogen, hydroxyl or alkoxy, as shown in Scheme 1. Such processes are disclosed, for example, in EP-A 0 90 062 and EP-B 0 186 117.

Scheme 1

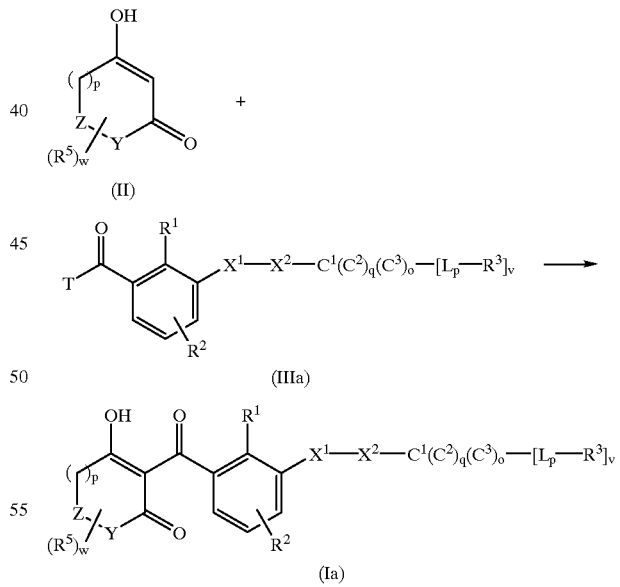

Compounds of the abovementioned formula (IIIa) can be prepared in accordance with methods known per se from compounds of the formulae (IIIb) and (IVa) in which $L^1$ is a leaving group such as halogen, mesyl, tosyl and triflate. Such methods are known, for example, from Houben-Weyl Volume 6/3, pp. 54 to 69, Volume 9, pp. 103 to 115 and Volume 11/1, p. 97.

Scheme 2

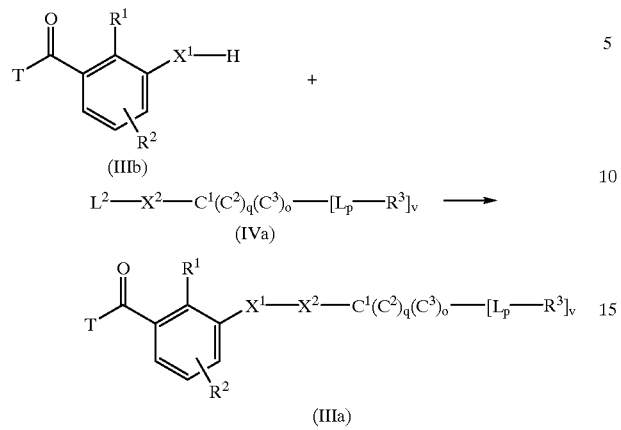

Compounds of the formula (IIIa) can also be prepared from compounds of the formulae (IIIc) and (IVb) for example in accordance with methods described in Scheme 3. Such methods are known from WO 98/42648, Houben-Weyl Volume 6/3, pp. 75 to 78, Volume 9, pp. 103 to 105.

Scheme 3

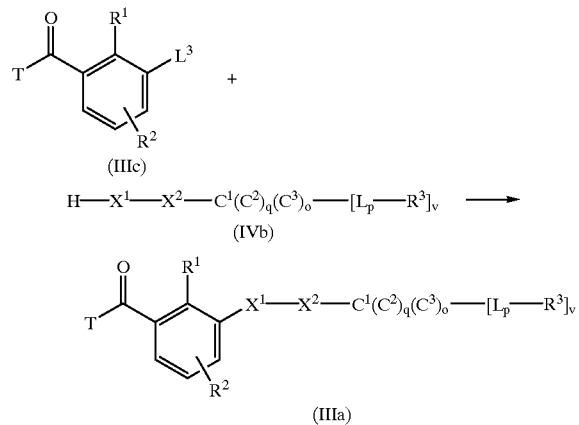

Compounds of the formula (I) according to the invention in which $R^4$ is radicals other than hydroxyl can be prepared for example according to Scheme 4. As shown therein, the reaction of a compound of the formula (Ia) with a halogenating reagent such as oxalyl chloride or oxalyl bromide yields compounds of the formula (Ib) according to the invention which can be reacted with nucleophiles, such as alkali metal cyanides, alkali metal cyanates, alkali metal thiocyanates, alkyl thioalcohols and thiophenols, if appropriate with base catalysis, to give further compounds of the formula (Ic) according to the invention in which $R^4$ is alkylthio, haloalkylthio, alkenylthio, haloalkenylthio, alkynylthio, haloalkynylthio, optionally substituted phenylthio, cyano, cyanato, thiocyanato or $OR^7$. Such reactions are described, for example, in Synthesis 12, 1287 (1992). Reaction with an oxidant such as m-chloroperoxybenzoic acid, peroxyacetic acid, hydrogen peroxide and potassium peroxymonosulfate gives compounds of the formula (Ic) according to the invention in which $R^4$ is alkylsulfinyl, haloalkylsulfinyl, alkenylsulfinyl, haloalkenylsulfinyl, alkynylsulfinyl, haloalkynylsulfinyl, alkylsulfonyl, haloalkylsulfonyl, alkenylsulfonyl, haloalkenylsulfonyl, alkynylsulfonyl, optionally substituted phenylthio or haloalkynylsulfonyl. Such reactions are described, for example, in *J. Org. Chem.* 53, 532 (1988), *Tetrahedron Lett.* 21, 1287 (1981).

Scheme 4

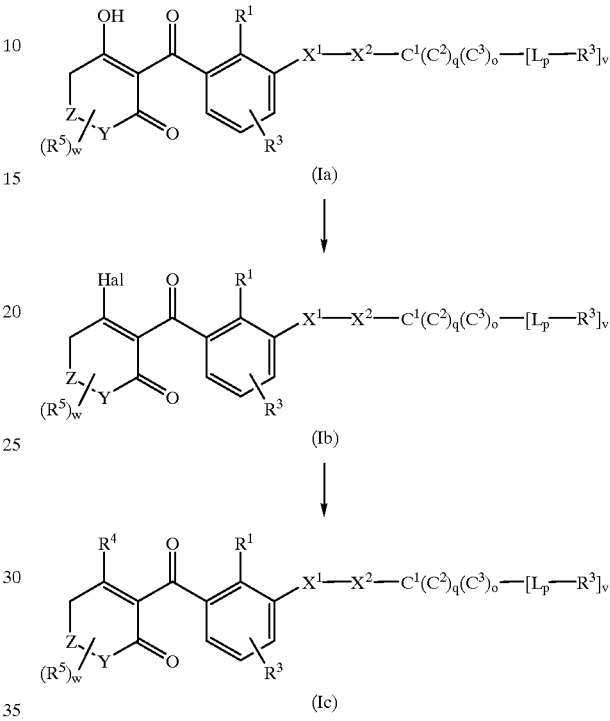

Compounds of the formulae (IIIa), with the exception of the compounds in which $C^1$ is oxiranyl or oxetanyl and the variable terms o and q are both zero, are novel and also subject matter of the invention.

The compounds of the formula (I) according to the invention have an outstanding herbicidal activity against a broad spectrum of economically important monocotyledonous and dicotyledonous harmful plants. The active substances also effect good control of perennial weeds which produce shoots from rhizomes, root stocks or other perennial organs and which are difficult to control. In this context, it is immaterial whether the substances are applied before sowing, pre-emergence or post-emergence. Specifically, some representatives of the monocotyledonous and dicotyledonous weed flora which can be controlled by the compounds according to the invention may be mentioned by way of example, without a restriction to certain species being intended to take place as a result of the mention. Amongst the monocotyledonous weed species, those on which the active substances act efficiently are, for example, *Avena, Lolium, Alopecurus, Phalaris, Echinochloa, Digitaria, Setaria* and *Cyperus* species from the annual group and, among the perennial species, *Agropyron, Cynodon, Imperata* and *Sorghum* and also perennial *Cyperus* species.

In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* among the annuals and *Convolvulus, Cirsium, Rumex* and *Artemisia* in the case of the perennial weeds. Harmful plants occurring under the specific cultivation conditions of rice such as, for example, Echinochloa, Sagittaria, Alisma, Eleocharis, Scirpus and Cyperus, are also outstandingly well controlled by the active substances according to the invention. If the compounds according to the invention are applied to the soil surface before germination, then the weed seedlings are either prevented completely from emerging or the weeds grow until they have reached the cotyledon stage, but then their growth stops and they finally die completely after three to four weeks have elapsed. When the active substances are applied post-emergence to the green parts of the plants, growth also stops drastically a very short time after the treatment and the weed plants remain at the stage of growth at the time of application, or they die completely after a certain time, so that in this manner competition by the weeds, which is harmful to the crop plants, is eliminated at a very early stage and in a sustained manner.

Although the compounds according to the invention have excellent herbicidal activity against monocotyledonous and dicotyledonous weeds, crop plants of economically important crops such as wheat, barley, rye, rice, maize, sugar beet, cotton and soybeans, are damaged only to an insignificant extent or not at all. For these reasons, the present compounds are very highly suitable for selectively controlling undesired vegetation in stands of agriculturally useful plants or in stands or ornamental plants.

On account of their herbicidal and plant growth-regulatory properties, the active substances can also be employed for controlling harmful plants in crops of known genetically modified plants or genetically modified plants yet to be developed. As a rule, the transgenic plants are distinguished by particularly advantageous properties, for example by resistances to certain pesticides, especially certain herbicides, resistances to plant diseases or plant pathogens, such as certain insects or microorganisms such as fungi, bacteria or viruses. Other particular properties relate, for example, to the harvested material with respect to quantity, quality, storability, composition and specific constituents. Thus, transgenic plants with an increased starch content or in which the quality of the starch is altered, or those having a different fatty acid composition of the harvested material, are known.

The compounds of the formula (I) according to the invention or their salts are preferably used in economically important transgenic crops of useful plants and ornamentals, e.g. of cereals such as wheat, barley, rye, oats, sorghum and millet, rice, cassava and maize, or else crops of sugar beet, cotton, soybeans, oil seed rape, potatoes, tomatoes, peas and other types of vegetable. The compounds of the formula (I) can preferably be employed as herbicides in crops of useful plants which are resistant, or have been made resistant by recombinant methods, to the phytotoxic effect of herbicides.

Traditional ways of generating novel plants which have modified characteristics in comparison with existing plants consist, for example, in traditional breeding methods and the generation of mutants. Alternatively, novel plants with modified characteristics can be generated using recombinant procedures (see, for example, EP-A-0221044, EP-A-0131624). For example, a number of cases have been described of recombinant modifications of crop plants for the purpose of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659), transgenic crop plants, for example cotton, with the capability of producing Bacillus thuringiensis toxins (Bt toxins) which make the plants resistant to certain pests (EP-A-0142924, EP-A-0193259), transgenic crop plants having a modified fatty acid composition (WO 91/13972).

A large number of molecular-biological techniques with which novel transgenic plants with modified properties can be generated are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423–431).

To carry out such recombinant manipulations, nucleic acid molecules which permit a mutagenesis or a sequence modification by recombination of DNA sequences can be introduced into plasmids. For example, it is possible with the aid of the abovementioned standard methods to carry out base exchanges, to remove subsequences or to add natural or synthetic sequences. Adapters or linkers may be added in order to link the DNA fragments to each other.

For example, plant cells with a reduced activity of a gene product can successfully be generated by expressing at least one suitable antisense RNA, a sense RNA to achieve a cosuppression effect or by expressing at least one suitably constructed ribozyme which specifically cleaves transcripts of the abovementioned gene product.

To this end, it is possible to use firstly DNA molecules which encompass all of the coding sequence of a gene product including any flanking sequences which may be present and secondly DNA molecules which only encompass parts of the coding sequence, it being necessary for these parts to be of sufficient length to cause an antisense effect in the cells. Also possible is the use of DNA sequences which have a high degree of homology with the coding sequences of a gene product which are not entirely identical thereto.

When expressing nucleic acid molecules in plants, the protein synthesized may be localized in any compartment of the plant cell. However, to achieve localization in a particular compartment, it is possible for example to link the coding region with DNA sequences which guarantee localization in a certain compartment. Sequences of this type are known to the person skilled in the art, (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give intact plants. In principle, the transgenic plants can be plants of any desired plant species, i.e. both monocotyledonous and dicotyledonous plants.

Transgenic plants are thus obtainable which have modified properties as a result of overexpression, suppression or inhibition of homologous (=natural) genes or gene sequences, or expression of heterologous (=foreign) genes or gene sequences.

The compounds according to the invention can preferably be employed in transgenic crops which are resistant to herbicides from the group of the sulfonylureas, glufosinate-ammonium or glyphosate-isopropylammonium and analogous active substances.

When the active substances according to the invention are used in transgenic crops, effects which are specific for application in the particular transgenic crop, for example a modified or specifically widened spectrum of action which can be controlled, altered application rates which can be employed for application, preferably good combining ability with the herbicides, to which the transgenic crop is resistant, and an effect on growth and yield of the transgenic crop plants, occur in addition to the effects against harmful plants which can be observed in other crops. Subject matter of the invention is therefore also the use of the compounds according to the invention as herbicides for controlling harmful plants in transgenic crop plants.

The substances according to the invention additionally also have outstanding growth-regulatory properties in crop plants. They engage in the plants' metabolism in a regulatory fashion and can thus be employed for the targeted control of plant constituents and for facilitating harvesting, such as, for example, triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since lodging can be reduced, or prevented completely, hereby.

The compounds according to the invention can be employed in the form of wettable powders, emulsifiable concentrates, sprayable solutions, dusts or granules in the customary preparations. Subject matter of the invention is therefore herbicidal and plant growth-regulatory agents comprising compounds of the formula (I).

The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspension (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Engineering], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, e.g. butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates can be water based or oil based. They can be prepared for example by wet-grinding by means of customary bead mills, if appropriate with addition of surfactants, as have already been listed for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see, for example methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products see, for example G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the auxiliaries which are conventional in each case, such as stickers, wetters, dispersants, emulsifiers, penetrants, preservatives, antifreeze agents, solvents, fillers, carriers, colorants, antifoams, evaporation inhibitors, and pH and viscosity regulators.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Active substances which can be employed in combination with the active substances according to the invention in mixed formulations or in the tank mix are, for example, known active substances as are described, for example, in Weed Research 26, 441–445 (1986) or "The Pesticide Manual", 11th edition, The British Crop Protection Council and the Royal Soc. of Chemistry, 1997 and literature cited therein. Herbicides which must be mentioned, and can be combined with the compounds of the formula (I), are, for example, the following active substances (note: the compounds are either designated by the common name according to the International Organization for Standardization (ISO) or using the chemical name, if appropriate together with a customary code number): acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluorine-2-phenyl-4H-3,1-benzoxazin4-one; benazolin; benfluralin; benfuresate; bensulfuronmethyl; bensulide; bentazone; benzofenap; benzofluor; benzoylpropethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)4,5-dihydro-5-oxo-1H-tetrazol-1-yl]phenyl]ethanesulfonamide; ethoxyfen and its esters (for example ethylester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentylester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methylester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester;

sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D489; LS 82–556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are present in commercially available form, are, if appropriate, diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use.

The application rate required of the compounds of the formula (I) varies with the external conditions such as, inter alia, temperature, humidity and the nature of the herbicide used. It can vary within wide limits, for example between 0.001 and 10.0 kg/ha or more of active substance, but it is preferably between 0.005 and 5 kg/ha.

The examples which follow illustrate the invention.

A. CHEMICAL EXAMPLES

1.1 Preparation of 2-(2-chloro-3-cyclopentylmethoxy-4-ethylsulfonylbenzoyl)cyclohexane-1,3-dione The compound 2-chloro-3-hydroxy-4-ethylsulfonylbenzoic acid which was used as starting material was prepared in accordance with the method described in EP-A 0 195 247. Ethyl 2,4-dibromo-3-hydroxybenzoate was prepared by the method described in U.S. Pat. No. 5,026,896. Cyclopentylcarbinyl methanesulfonate was prepared as described in J. Org. Chem 45, 9 (1980) 1707–1708.

Step 1: Methyl 2-chloro-3-hydroxy4-ethylsulfonylbenzoate 33.0 g (124.7 mmol) of 2-chloro-3-hydroxy-4-ethylsulfonylbenzoic acid were dissolved in 1 300 ml of methanol. 174 ml (3 263 mmol) of concentrated $H_2SO_4$ were added dropwise and the mixture was refluxed for 5 hours. The reaction mixture was evaporated on a rotary evaporator and the residue was taken up in methylene chloride. The mixture was washed with water, dried over $Na_2SO_4$ and evaporated completely on a rotary evaporator. This gave methyl 2-chloro-3-hydroxy-4-ethylsulfonylbenzoate as yellow viscous oil.

Yield: 28.23 g (81% of theory) Rf (ethyl acetate) 0.45 $^1$H NMR: $\delta$[CDCl$_3$] 1.32 (t, 3H), 3.24 (q, 2H), 3.96 (s, 3H), 7.38 (d, 1H), 7.65 (d, 1H)

Step 2: Methyl 2-chloro-3-cyclopentylmethoxy-4-ethylsulfonylbenzoate 1.488 g (10.8 mmol) of potassium carbonate and 1.343 g (7.5 mmol) of cyclopentylcarbinyl methanesulfonate were introduced into 30 ml of N,N-dimethylformamide. 1.50 g (5.4 mol) of methyl 2-chloro-3-hydroxy-4-ethylsulfonylbenzoate were added at room temperature and the mixture was heated for 5 hours at 70–80° C. The mixture was subsequently poured into water and extracted with diethyl ether. The combined organic phases were washed with water, dried over $Na_2SO_4$ and evaporated completely on a rotary evaporator. Drying in an oil pump vacuum gave methyl 2-chloro-3-cyclopentylmethoxy-4-ethylsulfonylbenzoate as brown oil.

Yield: 1.10 g (56% of theory) Rf (ethyl acetate) 0.77 $^1$H NMR: $\delta$[CDCl$_3$] 1.23 (t, 3H), 1.43 (m, 2H), 1.63 (m, 4H), 1.84 (m, 2H), 2.51 (m, 1H), 3.43 (q, 2H), 3.95 (s, 3H), 4.13 (d, 2H), 7.60 (d, 1H), 7.89 (d, 1H)

Step 3: 2-Chloro-3-cyclopentylmethoxy-4-ethylsulfonylbenzoic acid 1.100 g (3.00 mmol) of methyl 2-chloro-3-cyclopentylmethoxy-4-ethylsulfonylbenzoate were dissolved in a mixture of 20 ml of tetrahydrofuran and 20 ml of water, and 0.134 g (3.40 mmol) of sodium hydroxide were added. The mixture was stirred for 12 h at room temperature and evaporated completely on a rotary evaporator. The residue was taken up in water and 6 N HCl was added. The resulting mixture was extracted twice with methylene chloride, dried over $Na_2SO_4$ and evaporated completely on a rotary evaporator. This gave 2-chloro-3-cyclopentylmethoxy-4-ethylsulfonylbenzoic acid in the form of a viscous oil.

Yield: 1.04 g (100% of theory) Rf (ethyl acetate) 0.59 $^1$H NMR: $\delta$[CDCl$_3$] 1.24 (t, 3H), 1.45 (m, 2H), 1.62 (m, 4H), 1.84 (m, 2H), 2.52 (m, 1H), 3.43 (q, 2H), 4.13 (d, 2H), 7.76 (d,1 H), 7.93 (d, 1H)

Step 4: 3-Oxo-1-cyclohexenyl-2-chloro-3-cyclopentylmethoxy-4-ethylsulfonylbenzoate 0.550 g (1.60 mmol) of 2-chloro-3-cyclopentylmethoxy-4-ethylsulfonylbenzoic acid, 0.196 g (1.70 mmol) of cyclohexane-1,3-dione, 0.279 g (1.40 mmol) of N'-(3-dimethylaminopropyl)-N-ethylcarbodiimide hydrochloride and 0.002 g of dimethylaminopyridine were stirred for 10 hours at room temperature in 15 ml of methylene chloride. The mixture was subsequently diluted with methylene chloride and washed with 0.5 N HCl, with water, with saturated $NaHCO_3$ solution and again with water. After the combined organic phases had been dried over $Na_2SO_4$ and evaporated completely on a rotary evaporator, 3-oxo-1-cyclohexenyl 2-chloro-3-cyclopentylmethoxy-4-ethylsulfonylbenzoate was obtained in the form of a brown resin.

Yield: 0.335 g (47% of theory) Rf (ethyl acetate): 0.68 $^1$H NMR: $\delta$[CDCl$_3$] 1.23 (t, 3H), 1.44 (m, 2H), 1.64 (m, 4H), 1.85 (m, 2H), 2.15 (m, 2H), 2.47 (m, 2H), 2.53 (m, 1H), 2.68 (m, 2H), 3.25 (q, 2H), 4.15 (d, 2H), 6.08 (s, 1H), 7.71 (d, 1H), 7.96 (d, 1H)

Step 5: 2-(2-Chloro-3-cyclopentylmethoxy-4-ethylsulfonylbenzoyl)-cyclohexane-1,3-dione 0.290 g (0.70 mmol) of 3-oxo-1-cyclohexenyl 2-chloro-3-cyclopentylmethoxy-4-ethylsulfonylbenzoate was dissolved in 10 ml of acetonitrile. 3 drops of acetone cyanohydrin and 0.117 g (1.20 mmol) of triethylamine were added. The mixture was stirred for 2 hours at room temperature whereupon 0.013 g (0.20 mmol) of potassium cyanide was added. After a further 10 hours at room temperture, the mixture was evaporated completely, and the residue was taken up in water and 6 N hydrochloric acid was added. The mixture was subsequently extracted with methylene chloride. After the combined organic phases had been dried over $Na_2SO_4$, evaporated completely on a rotary evaporator and chromatographed on reversed-phase silica gel (mobile phase: acetonitrile/water gradient), 2-(2-chloro-3-cyclopentylmethoxy-4-ethylsulfonylbenzoyl)cyclohexane-1,3-dione was obtained in the form of a colourless viscous oil.

Yield: 0.175 g (57% of theory) Rf (ethyl acetate): 0.50 $^1$H NMR: δ[CDCl$_3$] 1.25 (t, 3H), 1.45 (m, 2H), 1.60 (m, 4H), 1.82 (m, 2H), 2.05 (m, 2H), 2.44 (m, 2H), 2.50 (m, 1H), 2.80 (m, 2H), 3.23 (q, 2H), 4.11 (d, 2H), 7.05 (d, 1H), 7.90 (d, 1H)

Preparation of 2-(2,4-dibromo-3-cyclobutylmethoxybenzoyl)-cyclohexane-1,3-dione

Step 1: Ethyl 2,4-dibromo-3-cyclobutylmethoxybenzoate 2.990 g (21.60 mmol) of potassium carbonate and 3.050 g (9.40 mmol) of ethyl 2,4-dibromo-3-hydroxybenzoate were introduced into 50 ml of N,N-dimethylformamide. 1.401 g (9.40 mmol) of bromomethylcyclobutane were added at room temperature and the mixture was heated for 6 hours at 120–130° C. The mixture was subsequently poured into water and extracted with diethyl ether. The combined organic phases were washed with water, dried over Na$_2$SO$_4$ and evaporated completely on a rotary evaporator. Drying in an oil-pump vacuum gave ethyl 2,4-dibromo-3-cyclobutylmethoxybenzoate as brown oil.

Yield: 3.10 g (85% of theory) Rf (ethyl acetate) 0.88 $^1$H NMR: δ[CDCl$_3$] 1.20 (t, 3H), 1.87–2.26 (m, 6H), 2.87 (m, 1H), 4.00 (d, 2H), 4.19 (q, 2H), 7.31 (d, 1H), 7.54 (d, 1H)

Step 2: 2,4-Dibromo-3-cyclobutylmethoxybenzoic acid 3.000 g (7.30 mmol) of ethyl 2,4-dibromo-3-(cyclobutylmethoxy)benzoate were dissolved in a mixture of 30 ml of tetrahydrofuran and 30 ml of water, and 0.436 g (10.90 mmol) of sodium hydroxide was added. The mixture was stirred for 12 hours at room temperature and evaporated completely on a rotary evaporator. The residue was taken up in water, and 6 N HCl was added. The mixture obtained was extracted twice with methylene chloride, dried over Na$_2$SO$_4$ and evaporated completely on a rotary evaporator. This gave 2,4-dibromo-3-cyclobutylmethoxybenzoic acid in the form of a viscous oil.

Yield: 2.50 g (94% of theory) Rf (ethyl acetate) 0.60 $^1$H NMR: δ[CDCl$_3$] 1.87–2.09 (m, 4H), 2.09–2.23 (m, 2H), 2.87 (m, 1H), 4.02 (d, 2H), 7.53 (d, 1H), 7.59 (d, 1H)

Step 3: 3-Oxo-1-cyclohexenyl 2,4-dibromo-3-cyclobutylmethoxybenzoate 1.150 g (3.20 mmol) of 2,4-dibromo-3-(cyclobutylmethoxy)benzoic acid, 0.39 g (3.50 mmol) of cyclohexane-1,3-dione, 0.618 g (3.20 mmol) of N'-(3-dimethylaminopropyl)-N-ethylcarbodiimide hydrochloride and 0.004 g of dimethylaminopyridine were stirred for 10 hours at room temperature in 30 ml of methylene chloride. The mixture was subsequently diluted with methylene chloride and washed with 0.5 N HCl, with water, with saturated NaHCO$_3$ solution and again with water. After the combined organic phases had been dried over Na$_2$SO$_4$ and evaporated completely on a rotary evaporator, 3-oxo-1-cyclohexenyl 2,4 dibromo-3-cyclobutylmethoxybenzoate was obtained in the form of a yellow resin.

Yield: 0.80 g (55% of theory) Rf (ethyl acetate): 0.88 $^1$H-NMR: δ[CDCl$_3$] 1.88–2.23 (m, 8H), 2.45 (m, 2H), 2.68 (m, 2H), 2.87 (m, 1H), 4.15 (d, 2H), 6.05 (s, 1H), 7.44 (d, 1H), 7.60 (d, 1H)

Step 4: 2-(2,4-Dibromo-3-(cyclobutylmethoxybenzoyl) cyclohexane-1,3-dione 0.220 g (0.50 mmol) 3-oxo-1-cyclohexenyl 2,4-dibromo-3-cyclobutylmethoxybenzoate was dissolved in 15 ml of acetonitrile. 3 drops of acetone cyanohydrin and 0.121 g (1.20 mmol) of triethylamine were added. The mixture was stirred for 2 hours at room temperature, whereupon 0.031 g (0.5 mmol) of potassium cyanide were added. After a further 10 hours at room temperature, the mixture was evaporated completely, the residue was taken up in water and 6 N hydrochloric acid was added. The mixture was subsequently extracted with methylene chloride. After the combined organic phases had been dried over Na$_2$SO$_4$, evaporated completely on a rotary evaporator and chromatographed on silica gel (mobile phase: toluene/THF), 2-(2,4-dibromo-3-cyclobutylmethoxybenzoyl)-cyclohexane-1,3-dione was obtained in the form of a colourless oil.

Yield: 0.10 g (44% of theory) Rf (ethyl acetate): 0.60 $^1$H NMR: δ[CDCl$_3$] 1.80–2.16 (m, 8H), 2.58 (m, 2H), 2.72 (m, 2H), 2.80 (m, 1H), 3.92 (d, 2H), 6.71 (d, 1H), 7.46 (d, 1H)

The examples listed in the tables which follow were prepared analogously to abovementioned methods or can be obtained analogously to abovementioned methods.

The abbreviations used have the following meanings:

Me = methyl
Ac = acetyl
i = iso
R$_f$ = retention value
Et = ethyl
Pr = propyl
c = cyclo
Ph = phenyl
t = tertiary
m.p. = melting point

TABLE 1

Compounds of the formula (I) according to the invention in which the substituents and symbols have the following meanings:
R$^1$ = Cl   R$^2$ = 4-SO$_2$Me   Y = CH$_2$   Z = CH$_2$   p = 1

(I)

[Structure of formula (I) showing cyclohexane-1,3-dione linked via carbonyl to substituted benzene ring with Cl, SO$_2$Me, and X$^1$—X$^2$—C$^1$(C$^2$)$_q$(C$^3$)$_o$—[L$_p$—R$^3$]$_v$ substituents; R$^5$ groups on cyclohexanedione ring]

| No. | X$^1$—X$^2$ | C$^1$(C$^2$)$_q$(C$^3$)$_o$—[L$_p$—R$^3$]$_v$ | R$^5$ | Physical Data |
|---|---|---|---|---|
| 1 | OCH$_2$ | 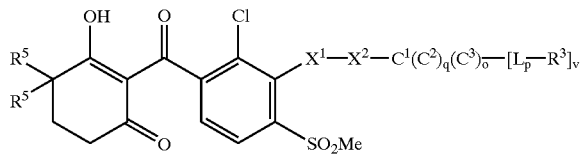 | H | Oil R$_f$: 0.53 (ethyl acetate) |

TABLE 1-continued

Compounds of the formula (I) according to the invention in which the substituents and symbols have the following meanings:

$R^1 = Cl \quad R^2 = 4\text{-}SO_2Me \quad Y = CH_2 \quad Z = CH_2 \quad p = 1$ $$\text{(I)}$$

| No. | $X^1$—$X^2$ | $C^1(C^2)_q(C^3)_o$—$[L_p$—$R^3]_v$ | $R^5$ | Physical Data |
|-----|-------------|-------------------------------------|-------|---------------|
| 2 | OCH$_2$ | cyclohexyl | Me | |
| 3 | OCH$_2$ | cyclohexyl-CH$_2$-CH=CH$_2$ | H | |
| 4 | OCH$_2$ | cyclohexyl-Cl | H | |
| 5 | OCH$_2$ | cyclohexyl-CN | H | |
| 6 | OCH$_2$ | cyclohexyl-CH$_2$CN | H | |
| 7 | OCH$_2$ | cyclohexyl-CH$_2$Cl | H | |
| 8 | OCH$_2$ | cyclohexyl-OMe | H | |
| 9 | OCH$_2$ | cyclohexyl-OMe | Me | |
| 10 | OCH$_2$ | cyclohexyl-NHEt | H | |

TABLE 1-continued
Compounds of the formula (I) according to the invention in which the substituents and symbols have the following meanings:
$R^1 = Cl$    $R^2 = 4\text{-}SO_2Me$    $Y = CH_2$    $Z = CH_2$    $p = 1$
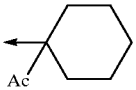
(I)
| No. | $X^1\text{—}X^2$ | $C^1(C^2)_q(C^3)_o\text{—}[L_p\text{—}R^3]_v$ | $R^5$ | Physical Data |
|---|---|---|---|---|
| 11 | $OCH_2$ | 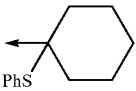 | H | |
| 12 | $OCH_2$ | 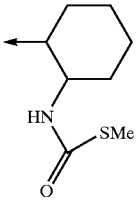 | H | |
| 13 | $OCH_2$ | 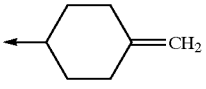 | H | |
| 14 | $OCH_2$ | 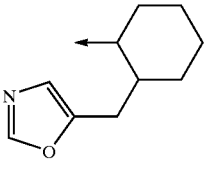 | H | |
| 15 | $OCH_2$ | 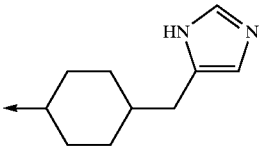 | H | |
| 16 | $OCH_2$ | 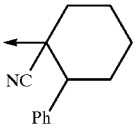 | H | |
| 17 | $OCH_2$ | 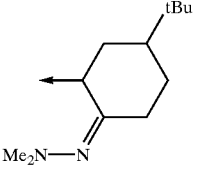 | H | |
| 18 | $OCH_2$ | 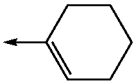 | H | |
| 19 | $OCH_2$— | | H | |

TABLE 1-continued

Compounds of the formula (I) according to the invention in which the substituents and symbols have the following meanings:
$R^1$ = Cl    $R^2$ = 4-SO$_2$Me    Y = CH$_2$    Z = CH$_2$    p = 1

(I)

| No. | $X^1$—$X^2$ | $C^1(C^2)_q(C^3)_o$—[$L_p$—$R^3$]$_v$ | $R^5$ | Physical Data |
|---|---|---|---|---|
| 20 | OCH$_2$ | cyclohexenyl | H | |
| 21 | OCH$_2$— | cyclohexenyl | H | Oil<br>$R_f$: 0.38 (ethyl acetate) |
| 22 | OCH$_2$ | cyclohexenyl | Me | |
| 23 | OCH$_2$— | 4-Me-cyclohexenyl | H | |
| 24 | OCH$_2$ | Me-cyclohexenyl | H | |
| 25 | OCH$_2$— | cyclohexenone | H | |
| 26 | OCH$_2$ | PhO$_2$S-cyclohexenyl | H | |
| 27 | OCH$_2$ | Me,Me-cyclohexenyl | H, H | |
| 28 | OCH$_2$ | Me,Ph-cyclohexenyl | H | |
| 29 | OCH$_2$ | pyrrolidinyl-cyclohexenone | H | |

TABLE 1-continued

Compounds of the formula (I) according to the invention in which the
substituents and symbols have the following meanings:
$R^1$ = Cl   $R^2$ = 4-SO$_2$Me   Y = CH$_2$   Z = CH$_2$   p = 1

$$\text{(I)}$$

| No. | $X^1$—$X^2$ | $C^1(C^2)_q(C^3)_o$—[$L_p$—$R^3$]$_v$ | $R^5$ | Physical Data |
|-----|-------------|---------------------------------------|-------|---------------|
| 30 | OCH$_2$CH$_2$ | cyclohexyl | H | |
| 31 | OCH$_2$CH$_2$ | cyclohexyl | Me | |
| 32 | OCH$_2$CH$_2$ | 2-methylenecyclohexyl (H$_2$C=) | H | |
| 33 | OCH$_2$CH$_2$ | 1-(allyl)cyclohexyl (H$_2$C=CH–CH$_2$–) | H | |
| 34 | OCH$_2$CH$_2$ | 1-methoxycyclohexyl (MeO) | H | |
| 35 | OCH$_2$CH$_2$ | 1-(phenylsulfonyl)cyclohexyl (PhO$_2$S) | H | |
| 36 | OCH$_2$CH$_2$ | 2-fluorocyclohexyl (F) | H | |
| 37 | OCH$_2$CH$_2$ | 2-(trifluoromethyl)cyclohexyl (F$_3$C) | H | |
| 38 | OCH$_2$CH$_2$CH$_2$ | 2-methoxycyclohexyl (MeO) | H | |
| 39 | OCH$_2$CH$_2$CH$_2$ | 2-(phenylamino)cyclohexyl (PhHN) | H | |

TABLE 1-continued

Compounds of the formula (I) according to the invention in which the substituents and symbols have the following meanings:
$R^1 = Cl$  $R^2 = 4\text{-}SO_2Me$  $Y = CH_2$  $Z = CH_2$  $p = 1$ (I)

| No. | $X^1\text{---}X^2$ | $C^1(C^2)_q(C^3)_o\text{---}[L_p\text{---}R^3]_v$ | $R^5$ | Physical Data |
|---|---|---|---|---|
| 40 | $OCH_2CH_2CH_2CH_2$ | cyclohexyl with OHC | H | |
| 41 | $OCH_2CH=CH$ | cyclohexyl with MeO, Me | H | |
| 42 | $OCH_2CH=CH$ | cyclohexyl with MeO, Me, Me | H | |
| 43 | $OCH_2CH=CH$ | cyclohexenyl | H | |
| 44 | $OCH_2C\equiv C$ | cyclohexyl with MeO, Me | H | |
| 45 | $OCH_2C\equiv C$ | cyclohexyl with MeO, Me, Me | H | |
| 46 | $OCH_2C\equiv C$ | cyclohexenyl | H | |
| 47 | $OCH_2$ | cyclopentyl | H | Oil $R_f$: 0.53 (ethyl acetate) |
| 48 | $OCH_2$ | cyclopentyl | Me | |
| 49 | $OCH_2$ | cyclopentyl with Me | H | |

TABLE 1-continued

Compounds of the formula (I) according to the invention in which the substituents and symbols have the following meanings:

$R^1 = Cl$  $R^2 = 4\text{-}SO_2Me$  $Y = CH_2$  $Z = CH_2$  $p = 1$

| No. | $X^1$—$X^2$ | $C^1(C^2)_q(C^3)_o$—$[L_p$—$R^3]_v$ | $R^5$ | Physical Data |
|---|---|---|---|---|
| 50 | OCH$_2$ | cyclopentyl-CH=CH$_2$ | H | |
| 51 | OCH$_2$ | cyclopentyl-Ph | H | |
| 52 | OCH$_2$ | cyclopentyl(Ph) | H | |
| 53 | OCH$_2$ | cyclopentyl-CH(Ph) | Me | |
| 54 | OCH$_2$ | cyclopentyl-CH(Ph) | H | |
| 55 | OCH$_2$ | cyclopentyl-SPh | H | |
| 56 | OCH$_2$ | cyclopentyl-SO$_2$Ph | H | |
| 57 | OCH$_2$ | cyclopentyl-NHC(O)NHMe | H | |
| 58 | OCH$_2$ | cyclopentyl-NHPh | H | |
| 59 | OCH$_2$ | 2-Me-4-Ph-cyclopentanone | H | |

TABLE 1-continued

Compounds of the formula (I) according to the invention in which the substituents and symbols have the following meanings:
$R^1$ = Cl  $R^2$ = 4-SO$_2$Me  Y = CH$_2$  Z = CH$_2$  p = 1

(I)

| No. | X$^1$—X$^2$ | C$^1$(C$^2$)$_q$(C$^3$)$_o$—[L$_p$—R$^3$]$_v$ | R$^5$ | Physical Data |
|---|---|---|---|---|
| 60 | OCH$_2$CH$_2$ | cyclopentyl | H | |
| 61 | OCH$_2$CH$_2$ | cyclopentyl-Et | H | |
| 62 | OCH$_2$CH$_2$ | cyclopentyl-Ph | H | |
| 63 | OCH$_2$CH$_2$CH$_2$ | cyclopentyl=CH$_2$ | H | |
| 64 | OCH$_2$CH$_2$CH$_2$ | cyclopentyl-PhNH | H | |
| 65 | OCH$_2$CH$_2$CH$_2$CH$_2$ | cyclopentanone | H | |
| 66 | OCH$_2$CH=CH | Me-cyclopentanone | H | |
| 67 | OCH$_2$C≡C | cyclopentyl-OMe | H | |
| 68 | OCH$_2$ | cyclopentenyl | H | |
| 69 | OCH$_2$ | cyclopentenyl | Me | |

TABLE 1-continued

Compounds of the formula (I) according to the invention in which the substituents and symbols have the following meanings:

$R^1 = Cl \quad R^2 = 4\text{-}SO_2Me \quad Y = CH_2 \quad Z = CH_2$ (I)

| No. | $X^1\text{—}X^2$ | $C^1(C^2)_q(C^3)_o\text{—}[L_p\text{—}R^3]_v$ | $R^5$ | Physical Data |
|-----|------------------|----------------------------------------------|-------|---------------|
| 70 | $OCH_2$ | cyclopentenyl | H | |
| 71 | $OCH_2$ | cyclopentadienyl | H | |
| 72 | $OCH_2$ | methyl-cyclopentenyl (Me) | H | |
| 73 | $OCH_2$ | Me, vinyl-CH$_2$-cyclopentenyl | H | |
| 74 | $OCH_2$ | cyclopentenyl with Et-CH= | H | |
| 75 | $OCH_2$ | cyclopentenyl-CH$_2$-CN | H | |
| 76 | $OCH_2$ | cyclopentenyl-NH-C(O)-Me | H | |
| 77 | $OCH_2$ | cyclopentenyl-NH-C(O)-O-tBu | H | |
| 78 | $OCH_2$ | n-Pr-substituted cyclopentenone | H | |

TABLE 1-continued

Compounds of the formula (I) according to the invention in which the substituents and symbols have the following meanings:

$R^1 = Cl \quad R^2 = 4\text{-}SO_2Me \quad Y = CH_2 \quad Z = CH_2 \quad p = 1$ (I)

| No. | $X^1\text{—}X^2$ | $C^1(C^2)_q(C^3)_o\text{—}[L_p\text{—}R^3]_v$ | $R^5$ | Physical Data |
|---|---|---|---|---|
| 79 | OCH$_2$CH$_2$ | cyclopentenyl | H | |
| 80 | OCH$_2$CH$_2$ | cyclopentenyl | Me | |
| 81 | OCH$_2$CH$_2$ | cyclopentenyl with Et-CH=CH substituent | H | |
| 82 | OCH$_2$CH$_2$CH$_2$ | cyclopentenyl-CH$_2$CH$_2$-Ph | H | |
| 83 | OCH$_2$CH$_2$CH$_2$CH$_2$ | cyclopentenone | H | |
| 84 | OCH$_2$CH=CH | cyclopentyl | H | |
| 85 | OCH$_2$C≡C | cyclopentyl | H | |
| 86 | CH$_2$C≡C | cyclopentenyl | Me | |
| 87 | OCH$_2$ | cyclobutyl | H | Oil, $R_f$: 0.54 (ethyl acetate) |
| 88 | OCH$_2$ | cyclobutyl | Me | |
| 89 | OCH$_2$ | cyclobutyl-Br | H | |
| 90 | OCH$_2$ | cyclobutyl-OMe | H | |

TABLE 1-continued
Compounds of the formula (I) according to the invention in which the substituents and symbols have the following meanings:
R¹ = Cl    R² = 4-SO₂Me    Y = CH₂    Z = CH₂    p = 1
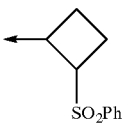
(I)
| No. | X¹—X² | C¹(C²)_q(C³)_o—[L_p—R³]_v | R⁵ | Physical Data |
|---|---|---|---|---|
| 91 | OCH₂ | 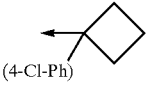 | H | |
| 92 | OCH₂ | 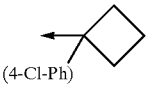 | H | |
| 93 | OCH₂ | 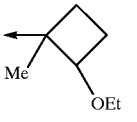 | Me | |
| 94 | OCH₂ |  | H | |
| 95 | OCH₂ | 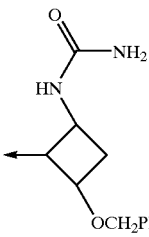 | H | |
| 96 | OCH₂ | 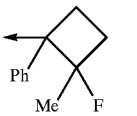 | H | |
| 97 | OCH₂ | 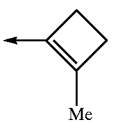 | H | |
| 98 | OCH₂ | 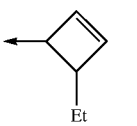 | H | |
| 99 | OCH₂ | | H | |

TABLE 1-continued

Compounds of the formula (I) according to the invention in which the substituents and symbols have the following meanings:
$R^1$ = Cl    $R^2$ = 4-SO$_2$Me    Y = CH$_2$    Z = CH$_2$    p = 1

$$\text{(I)}$$

| No. | $X^1$—$X^2$ | $C^1(C^2)_q(C^3)_o$—$[L_p$—$R^3]_v$ | $R^5$ | Physical Data |
|---|---|---|---|---|
| 100 | OCH$_2$CH$_2$ | cyclobutyl-Et | H | |
| 101 | OCH$_2$CH$_2$ | Me,Me-cyclobutyl-C(=CH$_2$) | H | |
| 102 | OCH$_2$CH$_2$ | tetrafluorocyclobutyl | H | |
| 103 | OCH$_2$CH$_2$ | cyclobutenyl | H | |
| 104 | OCH$_2$CH$_2$CH$_2$ | Me,Me-cyclobutyl-NHC(O)Me | H | |
| 105 | OCH$_2$C≡C | Me-cyclobutenyl | H | |
| 106 | OCH$_2$ | cyclopropyl | H | Oil $R_f$: 0.45 (ethyl acetate) |
| 107 | OCH$_2$ | cyclopropyl | Me | Oil $R_f$: 0.37 (ethyl acetate) |
| 108 | OCH$_2$ | Me-cyclopropyl | H | Oil $R_f$: 0.43 (ethyl acetate) |
| 109 | OCH$_2$ | Me-cyclopropyl | H | |
| 110 | OCH$_2$ | Cl-cyclopropyl | H | |

TABLE 1-continued
Compounds of the formula (I) according to the invention in which the substituents and symbols have the following meanings:
$R^1 = Cl$    $R^2 = 4\text{-}SO_2Me$    $Y = CH_2$    $Z = CH_2$    $p = 1$
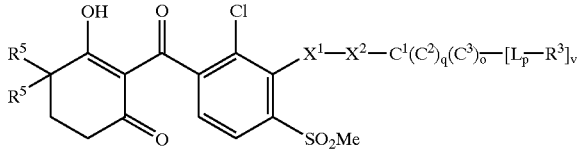
| No. | $X^1\text{---}X^2$ | $C^1(C^2)_q(C^3)_o\text{---}[L_p\text{---}R^3]_v$ | $R^5$ | Physical Data |
|---|---|---|---|---|
| 111 | OCH$_2$ | 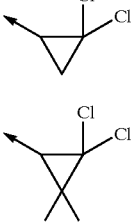 | H | Oil<br>$R_f$: 0.51 (ethyl acetate) |
| 112 | OCH$_2$ | 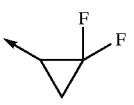 | H | |
| 113 | OCH$_2$ | 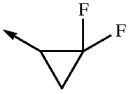 | H | |
| 114 | OCH$_2$ | 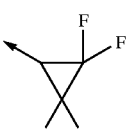 | Me | |
| 115 | OCH$_2$ | 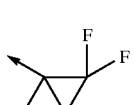 | H | |
| 116 | OCH$_2$ | 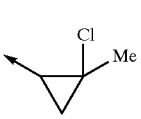 | H | |
| 117 | OCH$_2$ | 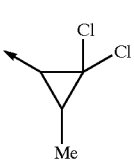 | H | |
| 118 | OCH$_2$ | 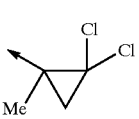 | H | |
| 119 | OCH$_2$ | 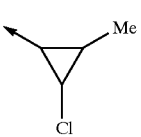 | H | |
| 120 | OCH$_2$ | | H | |

TABLE 1-continued
Compounds of the formula (I) according to the invention in which the substituents and symbols have the following meanings:
R¹ = Cl    R² = 4-SO₂Me    Y = CH₂    Z = CH₂
(I)
| No. | X¹—X² | C¹(C²)q(C³)o—[Lp—R³]v | R⁵ | Physical Data |
|-----|-------|------------------------|-----|---------------|
| 121 | OCH₂ |  n-Pr | H | |
| 122 | OCH₂ | CN | H | |
| 123 | OCH₂ | NO₂ | H | |
| 124 | OCH₂ | CH₂CN | H | |
| 125 | OCH₂ | Ph | H | |
| 126 | OCH₂ | Ph | H | |
| 127 | OCH₂ |  | H | |
| 128 | OCH₂ | i-Pr | H | |
| 129 | OCH₂ | SPh | H | |
| 130 | OCH₂ | SO₂Ph | H | |
| 131 | OCH₂ | SO₂Ph | Me | |
| 132 | OCH₂ | tBu (C=O) | H | |

TABLE 1-continued

Compounds of the formula (I) according to the invention in which the substituents and symbols have the following meanings:
$R^1$ = Cl   $R^2$ = 4-SO$_2$Me   Y = CH$_2$   Z = CH$_2$   p = 1

(I)

| No. | $X^1$—$X^2$ | $C^1(C^2)_q(C^3)_o$—[$L_p$—$R^3$]$_v$ | $R^5$ | Physical Data |
|---|---|---|---|---|
| 133 | OCH$_2$ | cyclopropyl-C(O)NH-CH(Me)-Ph | H | |
| 134 | OCH$_2$ | 1-cyanocyclopropyl-N(4-Ph-oxazolidine) | H | |
| 135 | OCH$_2$CH$_2$ | cyclopropyl | H | Oil R$_f$: 0.61 (ethyl acetate) |
| 136 | OCH$_2$CH$_2$ | cyclopropyl | Me | |
| 137 | OCH$_2$CH$_2$ | 2-Et-cyclopropyl | H | |
| 138 | OCH$_2$CH$_2$ | 2-Ph-cyclopropyl | H | |
| 139 | OCH$_2$CH$_2$ | 2-methylenecyclopropyl | H | |
| 140 | OCH$_2$CH$_2$ | 2-(1-methylethenyl)cyclopropyl | H | |
| 141 | OCH$_2$CH$_2$ | 2,2-dibromocyclopropyl | H | |
| 142 | OCH$_2$CH$_2$ | 2,2-difluoro-1-methylcyclopropyl | H | |
| 143 | OCH$_2$CH$_2$CH$_2$ | 2-Ph-cyclopropyl | H | |

TABLE 1-continued
Compounds of the formula (I) according to the invention in which the substituents and symbols have the following meanings:
$R^1 = Cl$   $R^2 = 4\text{-}SO_2Me$   $Y = CH_2$   $Z = CH_2$   $p = 1$
(I)
| No. | $X^1$—$X^2$ | $C^1(C^2)_q(C^3)_o$—$[L_p$—$R^3]_v$ | $R^5$ | Physical Data |
|---|---|---|---|---|
| 144 | OCH$_2$CH$_2$CH$_2$ | 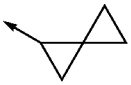 | H | |
| 145 | OCH$_2$CH=CH | 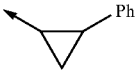 | H | |
| 146 | OCH$_2$CH$_2$ |  | H | |
| 147 | OCH$_2$ |  | H | |
| 148 | OCH$_2$ | 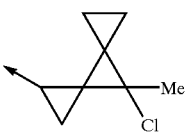 | H | |
| 149 | OCH$_2$ | 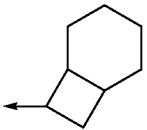 | H | |
| 150 | OCH$_2$ |  | H | |
| 151 | OCH$_2$ | 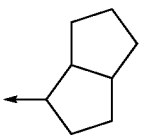 | H | |
| 152 | OCH$_2$CH$_2$ | 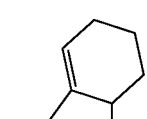 | H | |
| 153 | OCH$_2$CH$_2$ | 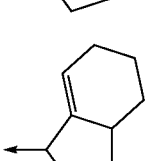 | H | |

TABLE 1-continued

Compounds of the formula (I) according to the invention in which the substituents and symbols have the following meanings:

$R^1$ = Cl  $R^2$ = 4-SO$_2$Me  Y = CH$_2$  Z = CH$_2$  p = 1

(I)

| No. | X$^1$—X$^2$ | C$^1$(C$^2$)$_q$(C$^3$)$_o$—[L$_p$—R$^3$]$_v$ | R$^5$ | Physical Data |
|---|---|---|---|---|
| 154 | OCH$_2$CH$_2$ | | H | |
| 155 | OCH$_2$ | (PhCH$_2$) | H | |
| 156 | OCH2 | | H | |
| 157 | OCH2 | | H | |
| 158 | OCH$_2$ | | H | |
| 159 | OCH$_2$ | | H | |
| 160 | OCH$_2$ | | H | |
| 161 | OCH$_2$ | | Me | |

TABLE 1-continued
Compounds of the formula (I) according to the invention in which the substituents and symbols have the following meanings:
$R^1$ = Cl   $R^2$ = 4-SO$_2$Me   Y = CH$_2$   Z = CH$_2$   p = 1
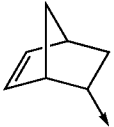
(I)
| No. | $X^1$—$X^2$ | $C^1(C^2)_q(C^3)_o$—$[L_p$—$R^3]_v$ | $R^5$ | Physical Data |
|---|---|---|---|---|
| 162 | OCH$_2$ | 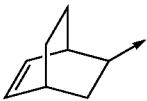 | H | |
| 163 | OCH$_2$ | 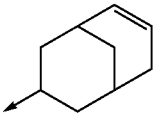 | H | |
| 164 | OCH$_2$ | 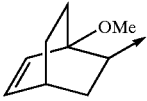 | H | |
| 165 | OCH$_2$CH$_2$ | 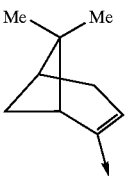 | H | |
| 166 | OCH$_2$CH$_2$ | 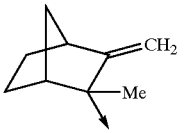 | H | |
| 167 | OCH$_2$CH$_2$CH$_2$ | 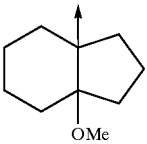 | H | |
| 168 | OCH$_2$CH$_2$CH$_2$CH$_2$ | 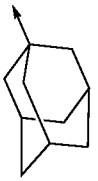 | H | |
| 169 | OCH$_2$CH$_2$ |  | H | |

TABLE 1-continued

Compounds of the formula (I) according to the invention in which the substituents and symbols have the following meanings:
$R^1 = Cl$   $R^2 = 4\text{-}SO_2Me$   $Y = CH_2$   $Z = CH_2$   $p = 1$ (I)

| No. | $X^1\text{—}X^2$ | $C^1(C^2)_q(C^3)_o\text{—}[L_p\text{—}R^3]_v$ | $R^5$ | Physical Data |
|---|---|---|---|---|
| 170 | $OCH_2CH_2$ | 1-bromoadamantyl | H | |

TABLE 2

Compounds of the formula (I) according to the invention in which the substituents and symbols have the following meanings:
$R^1 = Cl$   $R^2 = 4\text{-}SO_2Me$   $Y = CH_2$   $Z = CH_2$   $p = 1$   $w = 0$

| No. | $X^1\text{—}X^2$ | $C^1(C^2)_q(C^3)_o\text{—}[L_p\text{—}R^3]_v$ | $R^4$ | Physical data |
|---|---|---|---|---|
| 1 | $OCH_2$ | cyclohexyl | $OC(O)\text{—}Ph$ | |
| 2 | $OCH_2$ | cyclohexyl | $OSO_2\text{—}Ph$ | |
| 3 | $OCH_2$ | cyclohexyl-NCCH$_2$ | $OC(O)\text{—}Ph$ | |
| 4 | $OCH_2$ | cyclohexyl-HNC(O)SMe | $OSO_2\text{—}Ph$ | |
| 5 | $OCH_2$ | cyclohexenyl | $OC(O)\text{—}Ph$ | |

TABLE 2-continued

Compounds of the formula (I) according to the invention in which the substituents and symbols have the following meanings:

$R^1 = Cl$  $R^2 = 4\text{-}SO_2Me$  $Y = CH_2$  $Z = CH_2$  $p = 1$  $w = 0$

| No. | $X^1$—$X^2$ | $C^1(C^2)_q(C^3)_o$—$[L_p$—$R^3]_v$ | $R^4$ | Physical data |
|---|---|---|---|---|
| 6 | $OCH_2$ | cyclohexenyl | S—Ph | |
| 7 | $OCH_2$ | cyclohexenyl-CH$_2$NHSO$_2$Me | OC(O)—Ph | |
| 8 | $OCH_2CH_2$ | cyclohexyl | OC(O)—Ph | |
| 9 | $OCH_2CH_2$ | cyclohexyl | $OSO_2$—Ph | |
| 10 | $OCH_2CH_2$ | 2-F-cyclohexyl | $OSO_2$—Ph | |
| 11 | $OCH_2CH_2$ | 2-F-cyclohexyl | S—Ph | |
| 12 | $OCH_2CH_2$ | 2-CF$_3$-cyclohexyl | OC(O)—Ph | |
| 13 | $OCH_2CH$=CH | cyclohexenyl | OC(O)—Ph | |
| 14 | $OCH_2$ | cyclopentyl | OC(O)—Ph | |
| 15 | $OCH_2$ | 2-Ph-cyclopentyl | $OSO_2$—Ph | |

TABLE 2-continued

Compounds of the formula (I) according to the invention in which the substituents and symbols have the following meanings:
$R^1 = Cl$  $R^2 = 4\text{-}SO_2Me$  $Y = CH_2$  $Z = CH_2$  $p = 1$  $w = 0$

| No. | $X^1\text{—}X^2$ | $C^1(C^2)_q(C^3)_o\text{—}[L_p\text{—}R^3]_v$ | $R^4$ | Physical data |
|---|---|---|---|---|
| 16 | $OCH_2$ | cyclopentyl-SO$_2$Ph | $OC(O)$—Ph | |
| 17 | $OCH_2CH_2$ | cyclopentyl | $OSO_2$—Ph | |
| 18 | $OCH_2CH_2$ | cyclopentyl-Et | $OC(O)$—Ph | |
| 19 | $OCH_2CH_2$ | cyclopentyl-Ph | $OSO_2$—Ph | |
| 20 | $OCH_2$ | cyclopentenyl | $OC(O)$—Ph | |
| 21 | $OCH_2$ | cyclopentenyl | $S$—Ph | |
| 22 | $OCH_2CH_2$ | cyclopentenyl | $OSO_2$—Ph | |
| 23 | $OCH_2$ | cyclobutyl | $OC(O)$—Ph | |
| 24 | $OCH_2$ | cyclobutyl | $OSO_2$—Ph | |
| 25 | $OCH_2$ | cyclobutyl | $S$—Ph | |
| 26 | $OCH_2$ | cyclobutyl-OMe | $OC(O)$—Ph | |
| 27 | $OCH_2$ | cyclobutyl-SO$_2$Ph | $OC(O)$—Ph | |

TABLE 2-continued

Compounds of the formula (I) according to the invention in which the substituents and symbols have the following meanings:
$R^1 = Cl$   $R^2 = 4\text{-}SO_2Me$   $Y = CH_2$   $Z = CH_2$   $p = 1$, $w = 0$

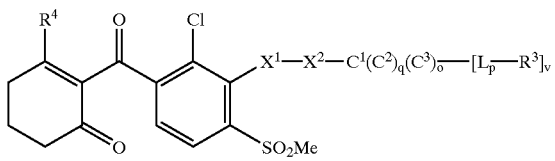

| No. | $X^1\text{—}X^2$ | $C^1(C^2)_q(C^3)_o\text{—}[L_p\text{—}R^3]_v$ | $R^4$ | Physical data |
|---|---|---|---|---|
| 28 | $OCH_2$ | cyclobutenyl-Me | $OSO_2$—Ph | |
| 29 | $OCH_2CH_2$ | cyclobutyl-Et | S—Ph | |
| 30 | $OCH_2CH_2$ | cyclobutyl-F,F,F,F | $OSO_2$—Ph | |
| 31 | $OCH_2C\equiv C$ | cyclobutenyl-Me | OC(O)—Ph | |
| 32 | $OCH_2$ | cyclopropyl | OC(O)—Ph | |
| 33 | $OCH_2$ | cyclopropyl | $OSO_2$—Ph | |
| 34 | $OCH_2$ | cyclopropyl | S—Ph | |
| 35 | $OCH_2$ | cyclopropyl-Me | OC(O)—Ph | |
| 36 | $OCH_2$ | cyclopropyl-Cl,Cl | S—Ph | |
| 37 | $OCH_2$ | cyclopropyl-F,F | OC(O)—Ph | |
| 38 | $OCH_2$ | cyclopropyl-Cl,Me | OC(O)—Ph | |
| 39 | $OCH_2$ | cyclopropyl-$NO_2$ | $OSO_2$—Ph | |

TABLE 2-continued

Compounds of the formula (I) according to the invention in which the substituents and symbols have the following meanings:
$R^1 = Cl$  $R^2 = 4\text{-}SO_2Me$  $Y = CH_2$  $Z = CH_2$  $p = 1$  $w = 0$

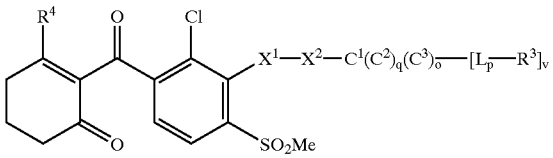

| No. | $X^1\text{—}X^2$ | $C^1(C^2)_q(C^3)_o\text{—}[L_p\text{—}R^3]_v$ | $R^4$ | Physical data |
|---|---|---|---|---|
| 40 | $OCH_2$ | cyclopropyl-cyclohexyl | $OSO_2\text{—}Ph$ | |
| 41 | $OCH_2CH_2$ | cyclopropyl | $OC(O)\text{—}Ph$ | |
| 42 | $OCH_2CH_2$ | cyclopropyl | $S\text{—}Ph$ | |
| 43 | $OCH_2CH\text{=}CH$ | cyclopropyl-Ph | $OC(O)\text{—}Ph$ | |
| 44 | $OCH_2CH_2$ | bicyclopropyl | $OSO_2\text{—}Ph$ | |
| 45 | $OCH_2$ | norbornenyl | $OC(O)\text{—}Ph$ | |

TABLE 3

Compounds of the formula (I) according to the invention in which the substituents and symbols have the following meanings:
$R^4 = OH$  $Y = CH_2$  $Z = CH_2$  $p = 1$  $w = 0$

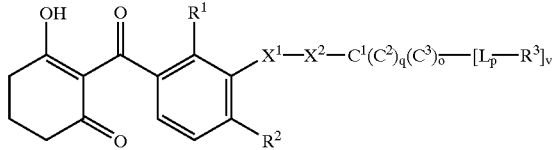

| No. | $R^1$ | $R^2$ | $X^1\text{—}X^2$ | $C^1(C^2)_q(C^3)_o\text{—}[L_p\text{—}R^3]_v$ | Physical data |
|---|---|---|---|---|---|
| 1 | Cl | Cl | $OCH_2$ | cyclohexyl | Oil $R_f$: 0.39 (ethyl acetate) |
| 2 | Br | Br | $OCH_2$ | cyclohexyl | Oil $R_f$: 0.47 (ethyl acetate) |

TABLE 3-continued

Compounds of the formula (I) according to the invention in which the substituents and symbols have the following meanings:

$R^4$ = OH   Y = $CH_2$   Z = $CH_2$   p = 1   w = 0

| No. | $R^1$ | $R^2$ | $X^1$—$X^2$ | $C^1(C^2)_q(C^3)_o$—[$L_p$—$R^3$]$_v$ | Physical data |
|---|---|---|---|---|---|
| 3 | Cl | $SO_2Et$ | $OCH_2$ | cyclohexyl | Oil $R_f$: 0.51 (ethyl acetate) |
| 4 | Me | $SO_2Me$ | $OCH_2$ | cyclohexyl | |
| 5 | Cl | Cl | $OCH_2$ | cyclohexyl–$NCCH_2$ | |
| 6 | Br | Br | $OCH_2$ | cyclohexyl–NHC(O)SMe | |
| 7 | Cl | Cl | $OCH_2$ | cyclohexenyl | Oil $R_f$: 0.17 (ethyl acetate) |
| 8 | Cl | $SO_2Et$ | $OCH_2$ | cyclohexenyl | Oil $R_f$: 0.48 (ethyl acetate) |
| 9 | Me | $SO_2Me$ | $OCH_2$ | cyclohexenyl | |
| 10 | Cl | $SO_2Et$ | $OCH_2$ | cyclohexenyl–$CH_2NHSO_2Me$ | |
| 11 | Cl | Cl | $OCH_2CH_2$ | cyclohexyl | |
| 12 | Cl | $SO_2Et$ | $OCH_2CH_2$ | cyclohexyl | |

TABLE 3-continued

Compounds of the formula (I) according to the invention in which the
substituents and symbols have the following meanings:
$R^4 = OH$   $Y = CH_2$   $Z = CH_2$   $p = 1$   $w = 0$

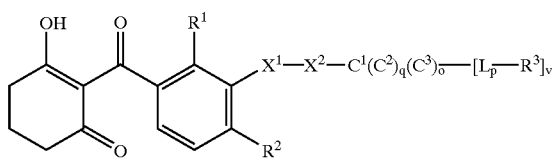

| No. | $R^1$ | $R^2$ | $X^1$—$X^2$ | $C^1(C^2)_q(C^3)_o$—$[L_p$—$R^3]_v$ | Physical data |
|---|---|---|---|---|---|
| 13 | Br | Br | OCH$_2$CH$_2$ | cyclohexyl-F | |
| 14 | Cl | Cl | OCH$_2$CH$_2$ | cyclohexyl-F | |
| 15 | Me | SO$_2$Me | OCH$_2$CH$_2$ | cyclohexyl-F | |
| 16 | Cl | SO$_2$Et | OCH$_2$CH$_2$ | cyclohexyl-CF$_3$ | |
| 17 | Cl | SO$_2$Et | OCH$_2$CH=CH | cyclohexenyl | |
| 18 | Cl | Cl | OCH$_2$ | cyclopentyl | Oil $R_f$: 0.68 (ethyl acetate) |
| 19 | Br | Br | OCH$_2$ | cyclopentyl | Oil $R_f$: 0.38 (ethyl acetate) |
| 20 | Cl | SO$_2$Et | OCH$_2$ | cyclopentyl | Oil $R_f$: 0.50 (ethyl acetate) |
| 21 | Me | SO$_2$Me | OCH$_2$ | cyclopentyl | |
| 22 | Cl | Cl | OCH$_2$ | cyclopentyl-Ph | |

TABLE 3-continued

Compounds of the formula (I) according to the invention in which the substituents and symbols have the following meanings:
R⁴ = OH    Y = CH₂    Z = CH₂    p = 1    w = 0

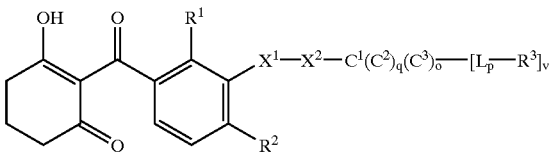

| No. | R¹ | R² | X¹—X² | C¹(C²)q(C³)o—[Lp—R³]v | Physical data |
|---|---|---|---|---|---|
| 23 | Br | Br | OCH₂ | cyclopentyl-Ph | |
| 24 | Me | SO₂Me | OCH₂ | cyclopentyl-Ph | |
| 25 | Cl | Cl | OCH₂ | cyclopentyl-SO₂Ph | |
| 26 | Br | Br | OCH₂ | cyclopentyl-SO₂Ph | |
| 27 | Cl | Cl | OCH₂CH₂ | cyclopentyl | |
| 28 | Cl | Cl | OCH₂CH₂ | cyclopentyl-Et | |
| 29 | Br | Br | OCH₂CH₂ | cyclopentyl-Ph | |
| 30 | Br | Br | OCH₂ | cyclopentenyl | |
| 31 | Cl | SO₂Et | OCH₂ | cyclopentenyl | |
| 32 | Cl | SO₂Et | OCH₂CH₂ | cyclopentenyl | |
| 33 | Cl | Cl | OCH₂ | cyclobutyl | Oil R_f: 0.58 (ethyl acetate) |
| 34 | Br | Br | OCH₂ | cyclobutyl | Oil R_f: 0.60 (ethyl acetate) |

TABLE 3-continued

Compounds of the formula (I) according to the invention in which the substituents and symbols have the following meanings:
$R^4 = OH \quad Y = CH_2 \quad Z = CH_2 \quad p = 1 \quad w = 0$

| No. | $R^1$ | $R^2$ | $X^1$—$X^2$ | $C^1(C^2)_q(C^3)_o$—$[L_p$—$R^3]_v$ | Physical data |
|---|---|---|---|---|---|
| 35 | Cl | SO$_2$Et | OCH$_2$ | cyclobutyl | Oil $R_f$: 0.53 (ethyl acetate) |
| 36 | Me | SO$_2$Me | OCH$_2$ | cyclobutyl | |
| 37 | Cl | SO$_2$Et | OCH$_2$ | cyclobutyl-OMe | |
| 38 | Cl | Cl | OCH$_2$ | cyclobutyl-SO$_2$Ph | |
| 39 | Cl | SO$_2$Et | OCH$_2$ | cyclobutenyl-Me | |
| 40 | Br | Br | OCH$_2$CH$_2$ | cyclobutyl-Et | |
| 41 | Cl | Cl | OCH$_2$CH$_2$ | tetrafluorocyclobutyl | |
| 42 | Cl | SO$_2$Et | OCH$_2$CH$_2$ | tetrafluorocyclobutyl | |
| 43 | Me | SO$_2$Me | OCH$_2$CH$_2$ | tetrafluorocyclobutyl | |
| 44 | Cl | Cl | OCH$_2$C≡C | cyclobutenyl-Me | |

TABLE 3-continued

Compounds of the formula (I) according to the invention in which the substituents and symbols have the following meanings:
R⁴ = OH    Y = CH₂    Z = CH₂    p = 1    w = 0

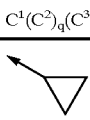

| No. | R¹ | R² | X¹—X² | C¹(C²)_q(C³)_o—[L_p—R³]_v | Physical data |
|-----|----|----|-------|---------------------------|---------------|
| 45 | Cl | Cl | OCH₂ | 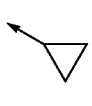 | Oil R_f: 0.20 (ethyl acetate) |
| 46 | Br | Br | OCH₂ |  | Oil R_f: 0.60 (ethyl acetate) |
| 47 | Cl | SO₂Et | OCH₂ |  | Oil |
| 48 | Me | SO₂Me | OCH₂ |  | |
| 49 | Cl | Cl | OCH₂ |  | Oil R_f: 0.57 (ethyl acetate) |
| 50 | Cl | SO₂Et | OCH₂ |  | Oil R_f: 0.23 (ethyl acetate) |
| 51 | Cl | Cl | OCH₂ |  | Oil R_f: 0.44 (ethyl acetate) |
| 52 | Br | Br | OCH₂ |  | Oil R_f: 0.40 (ethyl acetate) |
| 53 | Cl | SO₂Et | OCH₂ |  | Oil R_f: 0.19 (ethyl acetate) |
| 54 | Me | SO₂Me | OCH₂ |  | |
| 55 | Cl | Cl | OCH₂ |  | |
| 56 | Cl | SO₂Et | OCH₂ |  | |
| 57 | Br | Br | OCH₂ | | |

TABLE 3-continued

Compounds of the formula (I) according to the invention in which the substituents and symbols have the following meanings:
$R^4 = OH \quad Y = CH_2 \quad Z = CH_2 \quad p = 1 \quad w = 0$

| No. | $R^1$ | $R^2$ | $X^1$—$X^2$ | $C^1(C^2)_q(C^3)_o$—$[L_p$—$R^3]_v$ | Physical data |
|---|---|---|---|---|---|
| 58 | Cl | SO$_2$Et | OCH$_2$ | cyclopropyl-NO$_2$ | |
| 59 | Cl | Cl | OCH$_2$ | cyclopropyl-cyclohexyl | |
| 60 | Cl | Cl | OCH$_2$CH$_2$ | cyclopropyl | Oil R$_f$: 0.58 (ethyl acetate) |
| 61 | Cl | SO$_2$Et | OCH$_2$CH$_2$ | cyclopropyl | Oil R$_f$: 0.60 (ethyl acetate) |
| 62 | Cl | SO$_2$Et | OCH$_2$CH=CH | cyclopropyl-Me | |
| 63 | Cl | Cl | OCH$_2$CH$_2$ | bicyclopropyl | |
| 64 | Cl | SO$_2$Et | OCH$_2$ | norbornenyl | |

Formulation Examples

1. Dusts

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert substance, 10 parts by weight of potassium ligno-sulfonate and 1 part by weight of sodium oleoylmethyltaurate as wetter and dispersant and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range, for example, approx. 255 to over 277° C.) and grinding the mixture in a friction ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-Dispersible Granules

Water-dispersible granules are obtained by mixing

| | | |
|---|---|---|
| 75 | parts by weight | of a compound of the formula (I), |
| 10 | " | of calcium lignosulfonate, |
| 5 | " | of sodium lauryl sulfate, |
| 3 | " | of polyvinyl alcohol and |
| 7 | " | of kaolin, | grinding the mixture in a pinned-disk mill and granulating the powder in a fluidized bed by spraying on water as granulating fluid.

| | | |
|---|---|---|
| Water-dispersible granules are also obtained by homogenizing and precomminuting | | |
| 25 | parts by weight | of a compound of the formula (I), |
| 5 | " | of sodium 2,2'-dinaphthylmethane-6,6'-disulfonate, |
| 2 | " | of sodium oleoylmethyltaurate, |
| 1 | " | of polyvinyl alcohol, |
| 17 | " | of calcium carbonate and |
| 50 | " | of water | in a colloid mill, subsequently grinding the mixture in a bead mill and atomizing and drying the suspension obtained in a spray tower by means of a single-substance nozzle.

C. Biological Examples

1. Herbicidal Action Pre-Emergence

Seeds of mono- and dicotyledonous harmful plants are put into sandy loam in cardboard pots and covered with soil. The compounds according to the invention, which are formulated in the form of wettable powders or emulsion concentrates, are then applied to the surface of the soil cover as an aqueous suspension or emulsion at an application rate of 600 to 800 I/ha (converted) at a rate of 1 kg of active substance or less per hectare (converted). After the treatment, the pots are placed in a greenhouse and kept under good growth conditions for the weeds. Visual scoring of the plant damage or emergence damage is carried out after the test plants have emerged after a test period of 3 to 4 weeks in comparison with untreated controls. For example, the compounds of Examples No. 2 and 34 of Table 3 show at least a 90% action against Stellaria media and Amaranthus retroflexus.

2. Herbicidal Action Post-Emergence

Seeds of mono- and dicotyledonous weeds are put into sandy loam in cardboard pots, covered with soil and grown in the greenhouse under good growth conditions. Two to three weeks after sowing, the test plants are treated in the three-leaf stage. The compounds according to the invention, which are formulated as wettable powders or as emulsion concentrates, are sprayed onto the green plant parts at a rate of 1 kg of active substance or less per hectare (converted) at a water application rate of 600 to 800 I/ha (converted). After the test plants have been left to stand in the greenhouse for 3 to 4 weeks under optimal growth conditions, the action of the compounds is scored in comparison with untreated controls. The compositions according to the invention also show a good herbicidal activity post-emergence against a broad spectrum of economically important mono- and dicotyledonous harmful plants. For example, the compounds of Examples No. 2 and 34 of Table 3 show an at least 90% action against Stellaria media.

3. Action Against Harmful Plants in Rice

Typical harmful plants in rice crops are grown in the greenhouse under paddy rice conditions (depth of the water: 2–3 cm). After the treatment with the formulated compounds according to the invention at a rate of 1 kg of active substance or less per hectare (converted), the test plants are placed in the greenhouse under optimal growth conditions and kept in this way during the entire test period. About three weeks after application, evaluation is carried out by means of visually scoring the plant damage in comparison with untreated controls. The compounds according to the invention have a very good herbicidal action against harmful plants. For example, the compounds of Examples No. 34 and 46 of Table 3 show an at least 90% action against Cyperus difformis and *Echinochloa crus galli*.

4. Crop Plant Tolerance

In further experiments in the greenhouse, seeds of a relatively large number of crop plants and mono- and dicotyledonous weeds are put in sandy loam and covered with soil. Some of the pots are immediately treated as described under item 1, while the remaining pots are placed in the greenhouse until the plants have developed two to three true leaves and then sprayed with the compounds of the formula (I) according to the invention at different rates as described under item 2. Four to five weeks after application and after the plants have remained in the greenhouse, it is found by means of visual scoring that the compounds according to the invention as a rule leave dicotyledonous crops such as, for example, soybean and sugar beet undamaged or almost undamaged pre- and post-emergence, even at high doses of active substance. Moreover, some substances also leave graminaceous crops such as, for example, barley, wheat and rice unharmed. In some cases, the compounds of the formula (I) show high selectivity and are therefore suitable for controlling vegetation, some of which is undesired, in agricultural crops

What is claimed is:

1. A compound of the formula (I) or a salt thereof

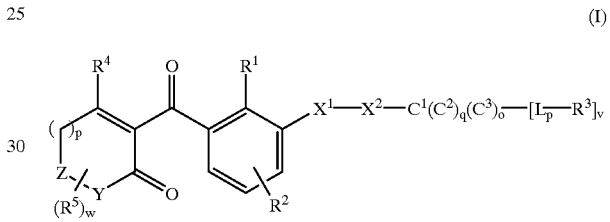

(I)

in which $X^1$ is a divalent unit selected from the group consisting of O, S(O)$_n$, NH, N[L$_p$-R$^3$];

$X^2$ is a straight-chain or branched (C$_1$–C$_6$)-alkylene, (C$_2$–C$_6$)-alkenylene or (C$_2$–C$_6$)-alkynylene chain which is substituted by w halogen atoms;

$C^1(C^2)_q(C^3)_o$ is a mono-, bi- or tricyclic radical, where
  e) the rings $C^1$, $C^2$ and $C^3$ are in each case a 3- to 8-membered, saturated or partially saturated ring selected from the group consisting of cycloalkyl, cycloalkenyl, oxiranyl and oxetanyl,
  f) the rings $C^1$, $C^2$ and $C^3$ are in each case linked to each other via one or two joint atoms;

$R^1$ and $R^2$ independently of one another are hydrogen, mercapto, nitro, cyano, halogen, thiocyanato, (C$_1$–C$_6$)-alkyl-CO—O, (C$_1$–C$_6$)-alkyl-S(O)$_n$—O, (C$_1$–C$_6$)-alkyl-S(O)$_n$, di-(C$_1$–C$_6$)-alkyl-NH—SO$_2$, (C$_1$–C$_6$)-allcyl-SO$_2$—NH, (C$_1$–C$_6$)-alkyl-NH—CO, (C$_1$–C$_6$)-alkyl-SO$_2$-[(C$_1$–C$_6$)-alkyl]amino, (C$_1$–C$_6$)-alkyl-CO—((C$_1$–C$_6$)-alkyl)amino, 1,2,4-triazol-1-yl, (C$_1$–C$_6$)-alkyl-O—CH$_2$, (C$_1$–C$_6$)-alkyl-S(O)$_n$—CH$_2$, (C$_1$–C$_6$)-alkyl-NH—CH$_2$, [(C$_1$–C$_6$)-alkyl]$_2$N—CH$_2$, 1,2,4-triazol-1-yl-CH$_2$, or are (C$_1$–C$_6$)-alkyl-(D)$_p$, (C$_2$–C$_6$)-alkenyl-(D)$_p$, (C$_2$–C$_6$)-alkynyl-(D)$_p$, (C$_3$–C$_9$)-cycloalkyl-(D)$_p$, (C$_3$–C$_9$)-cycloalkenyl-(D)$_p$, (C$_1$–C$_6$)-alkyl-(C$_3$–C$_9$)-cycloalkyl-(D)$_p$ or (C$_1$–C$_6$)-alkyl-(C$_3$–C$_9$)-cycloalkenyl-(D)$_p$, each of which is substituted by v radicals selected from the group consisting of cyano, nitro and halogen;

$R^3$ is hydrogen, hydroxyl, halogen, mercapto, amino, nitro, a carbon-containing radical or, if p in $X^1$ is zero, $R^3$ is oxo, NR$^8$, N—OR$^8$ or N—NR$^8$R$^9$;

D is oxygen or sulfur;

L is in each case straight-chain or branched $A_p$-[C($R^6$)$_2$]$_w$-[$A_p$-C($R^6$)$_2$]$_x$-$A_p$ or $A_p$-M-$A_p$ with the proviso that 2 or 3 of the variable terms p, w and x shall not simultaneously be zero;

A is a divalent unit selected from the group consisting of O, S(O)$_n$, NH, N—(C$_1$–C$_6$)-alkyl, N—(C$_2$–C$_6$)-alkenyl and N—(C$_2$–C$_6$)-alkynyl;

M is (C$_1$–C$_6$)-alkylene, (C$_2$–C$_6$)-alkenylene or (C$_2$–C$_6$)-alkynylene, each of which is substituted by w radicals $R^6$;

$R^4$ is $OR^7$, (C$_1$–C$_4$)-alkylthio, halo-(C$_1$–C$_4$)-alkylthio, (C$_1$–C$_4$)-alkenylthio, halo-(C$_2$–C$_4$)-alkenylthio, (C$_2$–C$_4$)-alkynylthio, halo-(C$_2$–C$_4$)-alkynylthio, (C$_2$–C$_4$)-alkylsulfinyl, halo-(C$_2$–C$_4$)-alkylsulfinyl, (C$_2$–C$_4$)-alkenylsulfinyl, halo-(C$_2$–C$_4$)-alkenylsulfinyl, (C$_2$–C$_4$)-alkynylsulfinyl, halo-(C$_2$–C$_4$)-alkynylsulfinyl, (C$_1$–C$_4$)-alkylsulfonyl, halo-(C$_1$–C$_4$-alkylsulfonyl, (C$_2$–C$_4$-alkenylsulfonyl, halo-(C$_2$–C$_4$)-alkenylsulfonyl, (C$_2$–C$_4$)-alkynylsulfonyl, halo-(C$_2$–C$_4$)-alkynylsulfonyl, cyano, cyanato, thiocyanato, halogen or phenylthio;

$R^5$ is hydrogen, tetrahydropyran-3-yl, tetrahydropyran-4-yl, tetrahydrothiopyran-3-yl, (C$_1$–C$_4$)-alkyl, (C$_3$–C$_8$)-cycloalkyl, (C$_1$–C$_4$)-alkoxy, (C$_1$–C$_4$-alkoxy-(C$_1$–C$_4$-alkyl, (C$_1$–C$_4$)-alkylcarbonyl, (C$_1$–C$_4$)-alkoxycarbonyl, (C$_1$–C$_4$)-alkylthio, phenyl, the eight last-mentioned groups being substituted by v radicals selected from the group consisting of halogen, (C$_1$–C$_4$)-alkylthio and (C$_1$–C$_4$)-alkoxy, or two radicals $R^5$ bonded to a joint carbon atom form a chain selected from the group consisting of OCH$_2$CH$_2$O, OCH$_2$CH$_2$CH$_2$O, SCH$_2$CH$_2$S and SCH$_2$CH$_2$CH$_2$S, this group being substituted by w methyl groups, or two radicals $R^5$ bonded to directly adjacent carbon atoms, together with the carbon atoms to which they are attached, form a 3- to 6-membered ring which is substituted by w radicals selected from the group consisting of halogen, (C$_1$–C$_4$)-alkyl, (C$_1$–C$_4$)-alkylthio and (C$_1$–C$_4$)-alkoxy;

$R^6$ is (C$_1$–C$_4$)-alkyl, halogen, cyano or nitro;

$R^7$ is hydrogen, (C$_1$–C$_4$)-alkyl, halo-(C$_1$–C$_4$)-alkyl, (C$_1$–C$_4$)-alkoxy-(C$_1$–C$_4$)-alkyl, formyl, (C$_1$–C$_4$-alkylcarbonyl, (C$_1$–C$_4$)-alkoxycarbonyl, (C$_1$–C$_4$)-alkylaminocarbonyl, di-(C$_1$–C$_4$-alkylaminocarbonyl, (C$_1$–C$_4$)-alkylsulfonyl, halo-(C$_1$–C$_4$)-alkylsulfonyl, benzoyl or phenylsulfonyl, the two last-mentioned groups being substituted by v radicals selected from the group consisting of (C$_1$–C$_4$)-alkyl, halo-(C$_1$–C$_4$)-alkyl, (C$_1$–C$_4$)-alkoxy, halo-(C$_1$–C$_4$)-alkoxy, halogen, cyano and nitro;

$R^8$ is hydrogen, (C$_1$–C$_4$)-alkyl, (C$_1$–C$_4$)-alkoxy, (C$_2$–C$_4$)-alkenyl, (C$_2$–C$_4$)-alkynyl, (C$_3$–C$_8$)-cycloalkyl, aryl, aryl-(C$_1$–C$_6$)-alkyl, heteroaryl, heterocyclyl, halo-(C$_1$–C$_4$)-alkyl;

$R^9$ is hydrogen, (C$_1$–C$_4$)-alkyl, (C$_2$–C$_4$)-alkenyl, (C$_2$–C$_4$)-alkynyl, (C$_3$–C$_9$)-cycloalkyl, aryl, aryl-(C$_1$–C$_6$)-alkyl, heteroaryl, heterocyclyl, halo-(C$_1$–C$_4$)-alkyl, or, if $R^8$ and $R^9$ are bonded to one atom or to two directly adjacent atoms, they together with the atoms to which they are bonded form a saturated, partially or fully unsaturated five- to six-membered ring which contains p hetero atoms selected from the group consisting of oxygen, nitrogen and sulfur;

Y is a divalent unit selected from the group consisting of O, S, N—H, N—(C$_1$–C$_4$)-alkyl, $CHR^5$ and C($R^5$)$_2$;

Z is a divalent unit selected from the group consisting of O, S, SO, SO$_2$, N—H, N—(C$_1$–C$_4$)-alkyl, $CHR^5$ and C($R^5$)$_2$;

m and n are each 0, 1 or 2;

o, p and q are each 0 or 1;

w and x are each 0, 1, 2, 3 or 4;

v is 0, 1, 2 or 3.

2. A benzoylcyclohexanedione as claimed in claim 1, in which $X^1$ is a divalent unit selected from the group consisting of O, S and NH;

$R^1$ is chlorine, bromine, fluorine, methyl, ethyl, cyano, nitro, halo-(C$_1$–C$_2$)-alkyl;

$R^2$ is halogen, halo-(C$_1$–C$_4$)-alkyl, (C$_1$–C$_4$)-alkylsulfenyl, (C$_1$–C$_4$)-alkylsulfinyl, (C$_1$–C$_4$)-alkylsulfonyl or nitro;

$R^5$ is (C$_1$–C$_4$)-alkyl, (C$_3$–C$_8$)-cycloalkyl, (C$_1$–C$_4$)-alkoxy, (C$_1$–C$_4$)-alkoxy-(C$_1$–C$_4$)-alkyl, (C$_1$–C$_4$)-alkylcarbonyl, (C$_1$–C$_4$)-alkoxycarbonyl, (C$_1$–C$_4$-alkylthio, phenyl, or two radicals $R^5$ bonded to a joint carbon atom form a chain selected from the group consisting of OCH$_2$CH$_2$O, OCH$_2$CH$_2$CH$_2$O, SCH$_2$CH$_2$S and SCH$_2$CH$_2$CH$_2$S, this group being substituted by w methyl groups, or two radicals $R^5$ bonded to directly adjacent carbon atoms form a bond or, together with the carbon atoms to which they are attached, form a 3- to 6-membered ring which is substituted by w radicals selected from the group consisting of halogen, (C$_1$–C$_4$)-alkyl, (C$_1$–C$_4$)-alkylthio and (C$_1$–C$_4$-alkoxy;

$R^8$ is hydrogen, (C$_1$–C$_4$)-alkyl, (C$_1$–C$_4$)-alkoxy, (C$_2$–C$_4$)-alkenyl, (C$_2$–C$_4$)-alkynyl, (C$_3$–C$_8$)-cycloalkyl, aryl, aryl-(C$_1$–C$_6$)-alkyl, halo-(C$_1$–C$_4$)-alkyl;

$R^9$ is hydrogen, (C$_1$–C$_4$)-alkyl, or, if $R^8$ and $R^9$ are bonded to one atom or to two directly adjacent atoms, they together with the atoms to which they are bonded form a saturated, partially or fully unsaturated five- to six-membered ring which contains p hetero atoms selected from the group consisting of oxygen, nitrogen and sulfur.

3. A benzoylcyclohexanedione as claimed in claim 1, in which $X^2$ is a straight-chain or branched (C$_1$–C$_4$)-alkylene, (C$_2$–C$_4$)-alkenylene or (C$_2$–C$_4$-alkynylene chain, each of which is substituted by w halogen atoms;

$R^3$ is a) hydrogen, hydroxyl, halogen, mercapto, amino, intro, cyano, formyl, b) phenyl, oxazolyl, furanyl or tetrahydropyrrolyl, each of which is substituted by w radicals selected from the group consisting of halogen, cyano, (C$_1$–C$_4$)-alkyl, halo-(C$_1$–C$_4$)-alkyl, (C$_1$–C$_4$)-alkoxy, halo-(C$_1$–C$_4$)-alkoxy, (C$_1$–C$_4$)-alkylthio, halo(C$_1$–C$_4$)-alkylthio and $R^{10}$, c) ($R^{11}$)(C$_1$–C$_4$)-alkylamino, ($R^{11}$)$_2$-amino $R^{11}$-oxycarbonyl, $R^{11}$-carbonyl, $R^{11}$-carbonyloxy, (C$_1$–C$_6$)-alkyl, (C$_2$–C$_6$)-alkenyl, (C$_2$–C$_6$)-alkynyl, (C$_1$–C$_6$)-alkoxy-(C$_1$–C$_6$)-alkyl, (C$_2$–C$_6$)-alkynyloxy-(C$_1$–C$_6$)-alkyl, (C$_3$–C$_9$)-cycloalkyl, (C$_3$–C$_9$)-cyloalkenyl, (C$_1$–C$_6$)-alkoxy or (C$_1$–C$_6$)-alkylthio, each of which is substituted by v radicals selected from the group consisting of formyl, halogen, cyano, intro, (C$_1$–C$_4$)-alkylamino, (C$_1$–C$_4$)-dialkylamino, (C$_1$–C$_4$)-alkoxycarbonyl, (C$_1$–C$_4$)-alkylcarbonyl, (C$_1$–C$_4$)-alkylcarbonyloxy, (C$_1$–C$_4$)-alkyl, (C$_2$–C$_4$)-alkenyl, $(C_2-C_4)$-alkynyl, halo-$(C_1-C_4)$-alkyl, $(C_1-C_4)$-alkylthio, halo-$(C_1-C_4$-alkylthio, $(C_1-C_4)$-alkoxy and halo-$(C_1-C_4$-alkoxy;

d) a radical of the formula Va, Vb, Vc, Vd, Vj or Vp, or e) if p is zero, then $R^3$ is oxo, $NR^8$, N—$OR^8$ or N—$NR^8R^9$;

$R^7$ is hydrogen, $(C_1-C_4)$-alkylsulfonyl, benzoyl or phenylsulfonyl, the two last-mentioned groups being substituted by v radicals selected from the group consisting of $(C_1-C_2)$-alkyl, halo-$(C_1-C_2)$-alkyl, $(C_1-C_2)$-alkoxy, halo-$(C_1-C_2)$-alkoxy, halogen, cyano and nitro, and $R^{11}$ is hydrogen, $(C_1-C_4)$-alkyl, $(C_2-C_4)$-alkenyl, $(C_2-C_4)$-alkynyl or $(C_3-C_8)$cycloalkyl.

4. A benzoylcyclohexanedione as claimed in claim 1, in which $X^1$ is the divalent unit O; $R^4$ is $OR^7$, $(C_1-C_4)$-alkylthio, $(C_2-C_4)$-alkenylthio, $(C_1-C_4)$-alkylsulfonyl, cyano, cyanato, thiocyanato, or else phenylthio which is substituted by v radicals selected from the group consisting of halogen, $(C_1-C_2)$-alkyl, $(C_1-C_2)$-alkoxy, halo-$(C_1-C_2)$alkyl, halo-$(C_1-C_2)$-alkoxy and nitro;

$R^5$ is hydrogen, $(C_1-C_4)$-alkyl, $(C_3-C_8)$-cycloalkyl, $(C_1-C_4)$-alkoxy, $(C_1-C_4)$-alkylthio, phenyl, or two radicals $R^5$ bonded to directly adjacent carbon atoms, together with the carbon atoms to which they are bonded, form a substituted 3- to 6-membered ring;

$R^{12}$ is hydrogen, $(C_1-C_4)$-alkyl, $(C_2-C_4)$-alkenyl, or, if $R^{11}$ and $R^{12}$ are bonded to one atom or to two directly adjacent atoms, they together with the atoms to which they are bonded form a saturated, partially or fully unsaturated five- to six-membered ring which contains p hetero atoms selected from the group consisting of oxygen, nitrogen and sulfur;

Y is a divalent unit selected from the group consisting of $CHR^5$ and $C(R^5)_2$, and Z is a divalent unit selected from the group consisting of O, S, $SO_2$, N—$(C_1-C_4)$alkyl, $CHR^5$ and $C(R^5)_2$.

5. A benzoylcyclohexanedione as claimed in claim 1, in which $R^2$ is halogen, halo-$(C_1-C_2)$-alkyl or $(C_1-C_2)$-alkylsulfonyl;

$R^5$ is $(C_1-C_4)$-alkyl, $(C_3-C_8)$-cycloalkyl, $(C_1-C_4)$-alkoxy, $(C_1-C_4)$-alkylthio, phenyl, or two radicals $R^5$ bonded to directly adjacent carbon atoms together with the carbon atoms to which they are attached form a substituted 3- to 6-membered ring;

$R^7$ is hydrogen, $(C_1-C_4)$-alkylsulfonyl, benzoyl or phenylsulfonyl, and $R^8$ is hydrogen, methyl or ethyl, and $R^2$ is in the 4-position of the phenyl ring.

6. A benzoylcyclohexanedione as claimed in claim 1, in which $X^2$ is a straight-chain or branched $(C_1-C_4)$-alkylene, $(C_2-C_4)$-alkenylene or $(C_2-C_4)$-alkynylene chain;

$R^1$ is chlorine, bromine, methyl, trifluoromethyl, cyano or nitro-;

$R^2$ is chlorine, bromine, methylsulfonyl, ethylsulfonyl, trifluoromethyl or nitro;

$R^4$ is $OR^7$, $(C_1-C_4)$-alkylthio, $(C_2-C_4)$-alkenylthio or phenylthio;

$R^5$ is hydrogen, $(C_1-C_4)$-alkyl, or two radicals $R^5$ bonded to directly adjacent carbon atoms together with the carbon atoms to which they are attached form a substituted 3- to 6-membered ring;

A is a divalent unit selected from the group consisting of O, $S(O)_n$, NH and N—$(C_1-C_6)$-alkyl;

M is $(C_1-C_6)$-alkylene;

Y and Z independently of one another are a divalent unit selected from the group consisting of $CHR^5$ and $C(R^5)_2$.

7. A herbicidal composition which comprises a herbicidally active content of at least one compound of the formula (I) as claimed in claim 1.

8. A herbicidal composition as claimed in claim 7 in mixture with formulation auxiliaries.

9. A method of controlling undesired plants, which comprise applying an effective amount of at least one compound of the formula (I) as claimed in claim 1 or of a herbicidal composition as claimed in claim 7 or 8 to the plants or to the site of the undesired plant growth.

10. The use of compounds of the formula (I) as claimed in claim 1 or of herbicidal compositions as claimed in claim 7 or 8 for controlling undesired plants.

11. The use as claimed in claim 10, wherein the compounds of the formula (I) are employed for controlling undesired plants in crops of useful plants.

12. The use as claimed in claim 11, wherein the useful plants are transgenic useful plants.

13. A method of controlling undesired plants, which comprises applying an effective amount of at least one compound of the formula (I) as claimed in claim 1 to the undesired plants or to the site of the undesired plant growth.

14. The method of claim 13, wherein the undesired plants are in crops of useful plants.

15. The method of claim 14, wherein the useful plants are transgenic.

16. A method of controlling undesired plants, which comprises applying an effective amount of a herbicidal composition as claimed in claim 7 or 8 to the undesired plants or to the site of the undesired plant growth.

17. The method of claim 16, wherein the undesired plants are in crops of useful plants.

18. The method of claim 17, wherein the useful plants are transgenic.

* * * * *